(12) United States Patent
Twite et al.

(10) Patent No.: US 12,161,158 B2
(45) Date of Patent: Dec. 10, 2024

(54) NON-NICOTINE POD ASSEMBLIES AND NON-NICOTINE E-VAPING DEVICES

(71) Applicant: Altria Client Services LLC, Richmond, VA (US)

(72) Inventors: Dean Twite, London (GB); Yannick Hourmand, Haslingfield (GB); Charles Dendy, Richmond, VA (US); Bipin Patil, Richmond, VA (US); Rangaraj S. Sundar, Midlothian, VA (US); Christopher Newcomb, Richmond, VA (US); Niall Gallagher, Cambridge (GB); Raymond W. Lau, Glen Allen, VA (US); Eric Hawes, Glen Allen, VA (US)

(73) Assignee: ALTRIA CLIENT SERVICES LLC, Richmond, VA (US)

(*) Notice: Subject to any disclaimer, the term of this patent is extended or adjusted under 35 U.S.C. 154(b) by 0 days.

(21) Appl. No.: 18/178,009

(22) Filed: Mar. 3, 2023

(65) Prior Publication Data

US 2023/0200442 A1  Jun. 29, 2023

Related U.S. Application Data

(63) Continuation of application No. 16/695,515, filed on Nov. 26, 2019, now Pat. No. 11,596,172.

(51) Int. Cl.
*A24F 40/42* (2020.01)
*A24F 15/06* (2006.01)
*A61M 15/06* (2006.01)

(52) U.S. Cl.
CPC ............. *A24F 40/42* (2020.01); *A61M 15/06* (2013.01)

(58) Field of Classification Search
CPC .......... A24F 40/10; A24F 40/40; A24F 40/42; A61M 15/06
See application file for complete search history.

(56) References Cited

U.S. PATENT DOCUMENTS

| | | | |
|---|---|---|---|
| 5,301,666 | A | 4/1994 | Lerk et al. |
| 6,810,883 | B2 | 11/2004 | Felter et al. |

(Continued)

FOREIGN PATENT DOCUMENTS

| | | |
|---|---|---|
| CN | 203646511 U | 6/2014 |
| CN | 203828084 U | 9/2014 |

(Continued)

OTHER PUBLICATIONS

International Search Report and Written Opinion for PCT/US2020/045692 dated Nov. 12, 2020.

(Continued)

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

A non-nicotine e-vaping device may include a non-nicotine pod assembly and a device body. The non-nicotine pod assembly has upstream and downstream ends and is configured to hold a non-nicotine pre-vapor formulation. The upstream end may define at least one upstream recess, and the downstream end may define at least one downstream recess. The device body defines a through hole configured to receive the non-nicotine pod assembly. The through hole includes an upstream sidewall and a downstream sidewall. The upstream sidewall may include at least one upstream protrusion, and the downstream sidewall may include at least one downstream protrusion. The at least one upstream protrusion and the at least one downstream protrusion may (Continued)

be configured to engage with the at least one upstream recess and the at least one downstream recess, respectively, so as to retain the non-nicotine pod assembly within the through hole of the device body.

11 Claims, 28 Drawing Sheets

(56) References Cited

U.S. PATENT DOCUMENTS

| | | | |
|---|---|---|---|
| D552,232 S | 10/2007 | Collins et al. | |
| 7,350,720 B2 | 4/2008 | Jaworski et al. | |
| 7,987,856 B2 | 8/2011 | Gedevanishvili et al. | |
| 8,291,898 B2 | 10/2012 | Southby et al. | |
| 8,424,540 B2 | 4/2013 | Olegario et al. | |
| 8,733,346 B2 | 5/2014 | Rinker | |
| 9,320,301 B2 | 4/2016 | Memari et al. | |
| 9,532,604 B2 | 1/2017 | Conley et al. | |
| 9,668,523 B2 | 6/2017 | Tucker et al. | |
| 9,750,284 B2 | 9/2017 | Rado | |
| 9,999,258 B2* | 6/2018 | Newcomb | G06F 21/44 |
| 10,028,537 B1 | 7/2018 | Hawes et al. | |
| 10,104,913 B2* | 10/2018 | Lau | H05B 1/0297 |
| 10,117,466 B2 | 11/2018 | Monsees et al. | |
| 10,779,572 B2* | 9/2020 | Mironov | A24F 40/46 |
| 11,123,501 B2* | 9/2021 | Nettenstrom | A61M 11/042 |
| 11,484,062 B2 | 11/2022 | Twite et al. | |
| 11,490,656 B2 | 11/2022 | Twite et al. | |
| 11,528,937 B2 | 12/2022 | Hourmand et al. | |
| 11,528,938 B2 | 12/2022 | Twite et al. | |
| 11,528,939 B2 | 12/2022 | Twite et al. | |
| 11,564,416 B2 | 1/2023 | Hourmand et al. | |
| 11,576,432 B2 | 2/2023 | Twite et al. | |
| 11,596,172 B2 | 3/2023 | Twite et al. | |
| 11,730,198 B2 | 8/2023 | Selby et al. | |
| 11,785,677 B2 | 10/2023 | Mironov et al. | |
| 2009/0241949 A1 | 10/2009 | Smutney et al. | |
| 2012/0199663 A1 | 8/2012 | Qiu | |
| 2013/0327327 A1* | 12/2013 | Edwards | A61M 15/0028 128/203.11 |
| 2014/0123989 A1 | 5/2014 | LaMothe | |
| 2014/0261487 A1 | 9/2014 | Chapman et al. | |
| 2015/0027457 A1 | 1/2015 | Janardhan et al. | |
| 2015/0101625 A1 | 4/2015 | Newton et al. | |
| 2015/0128971 A1 | 5/2015 | Verleur et al. | |
| 2015/0189919 A1* | 7/2015 | Liu | A24F 40/40 131/329 |
| 2015/0208729 A1 | 7/2015 | Monsees et al. | |
| 2015/0342255 A1 | 12/2015 | Wu | |
| 2015/0342258 A1 | 12/2015 | Chen | |
| 2015/0351456 A1 | 12/2015 | Johnson et al. | |
| 2015/0374039 A1 | 12/2015 | Zhu | |
| 2016/0021933 A1 | 1/2016 | Thorens et al. | |
| 2016/0050975 A1 | 2/2016 | Worm et al. | |
| 2016/0120226 A1 | 5/2016 | Rado | |
| 2016/0309787 A1 | 10/2016 | Hawes et al. | |
| 2016/0309788 A1 | 10/2016 | Hawes et al. | |
| 2016/0309789 A1 | 10/2016 | Thomas, Jr. | |
| 2016/0324216 A1 | 11/2016 | Li et al. | |
| 2016/0345626 A1 | 12/2016 | Wong et al. | |
| 2016/0360789 A1 | 12/2016 | Hawes et al. | |
| 2016/0374399 A1 | 12/2016 | Monsees et al. | |
| 2017/0027227 A1 | 2/2017 | Lipowicz | |
| 2017/0035115 A1 | 2/2017 | Monsees et al. | |
| 2017/0042246 A1* | 2/2017 | Lau | H05B 1/0227 |
| 2017/0071249 A1 | 3/2017 | Ampolini et al. | |
| 2017/0071253 A1 | 3/2017 | Revell | |
| 2017/0095624 A1 | 4/2017 | Davidson et al. | |
| 2017/0135409 A1 | 5/2017 | Cameron | |
| 2017/0150753 A1 | 6/2017 | Macko | |
| 2017/0172209 A1 | 6/2017 | Saydar et al. | |
| 2017/0197044 A1 | 7/2017 | Buchberger | |
| 2017/0202265 A1 | 7/2017 | Hawes et al. | |
| 2017/0231281 A1 | 8/2017 | Hatton et al. | |
| 2017/0231282 A1 | 8/2017 | Bowen et al. | |
| 2017/0258134 A1* | 9/2017 | Kane | H05B 3/56 |
| 2018/0020736 A1 | 1/2018 | Silvestrini et al. | |
| 2018/0027879 A1 | 2/2018 | Gavrielov et al. | |
| 2018/0104214 A1 | 4/2018 | Raichman | |
| 2019/0099562 A1 | 4/2019 | Nettenstrom et al. | |
| 2019/0104763 A1 | 4/2019 | Tucker et al. | |
| 2019/0104764 A1 | 4/2019 | Tucker et al. | |
| 2019/0142071 A1* | 5/2019 | Seok | A24F 40/46 131/329 |
| 2019/0166913 A1 | 6/2019 | Trzecieski | |
| 2019/0208820 A1 | 7/2019 | Reevell | |
| 2019/0254345 A1* | 8/2019 | Hepworth | A61M 11/042 |
| 2019/0274362 A1 | 9/2019 | Newcomb et al. | |
| 2019/0335813 A1* | 11/2019 | Qiu | A24F 40/485 |
| 2020/0114095 A1 | 4/2020 | Holroyd et al. | |
| 2020/0360628 A1* | 11/2020 | Mui | A61M 16/06 |
| 2020/0376210 A1 | 12/2020 | Simpson et al. | |
| 2020/0397046 A1 | 12/2020 | Lin et al. | |
| 2021/0045456 A1 | 2/2021 | Weigensberg et al. | |
| 2021/0068458 A1* | 3/2021 | Lomas | A24F 40/46 |
| 2021/0153548 A1 | 5/2021 | Twite et al. | |
| 2021/0153549 A1 | 5/2021 | Twite et al. | |
| 2021/0153566 A1 | 5/2021 | Hourmand et al. | |
| 2021/0153567 A1 | 5/2021 | Twite et al. | |
| 2021/0153568 A1 | 5/2021 | Twite et al. | |
| 2021/0153569 A1 | 5/2021 | Twite et al. | |
| 2021/0268215 A1 | 9/2021 | Israel et al. | |
| 2021/0337878 A1* | 11/2021 | Gretton | A24F 40/53 |
| 2022/0142257 A1* | 5/2022 | Austin | A24F 40/30 |
| 2023/0070448 A1 | 3/2023 | Twite et al. | |
| 2023/0111093 A1 | 4/2023 | Twite et al. | |
| 2023/0123679 A1 | 4/2023 | Twite et al. | |
| 2023/0124928 A1 | 4/2023 | Hourmand et al. | |
| 2023/0172268 A1 | 6/2023 | Hourmand et al. | |
| 2023/0189886 A1 | 6/2023 | Twite et al. | |

FOREIGN PATENT DOCUMENTS

| | | |
|---|---|---|
| CN | 207011683 U | 2/2018 |
| CN | 108741232 A | 11/2018 |
| CN | 108851243 A | 11/2018 |
| CN | 208692311 U | 4/2019 |
| CN | 208692313 U | 4/2019 |
| CN | 110461175 A | 11/2019 |
| EP | 3560360 A1 | 10/2019 |
| EP | 3569073 A1 | 11/2019 |
| JP | 2019-527049 A | 9/2019 |
| RU | 2017134972 A | 4/2019 |
| WO | WO-2016/079152 A1 | 5/2016 |
| WO | WO-2016/096780 A1 | 6/2016 |
| WO | WO-2016/172023 A1 | 10/2016 |
| WO | WO-2016/172802 A1 | 11/2016 |
| WO | WO-2017/102969 A1 | 6/2017 |
| WO | WO-2017/153597 A1 | 9/2017 |
| WO | WO-2017/163045 A1 | 9/2017 |
| WO | WO-2017/163052 A1 | 9/2017 |
| WO | WO-2017/207443 A1 | 12/2017 |
| WO | WO-2018/125674 A1 | 7/2018 |
| WO | WO-2018/217440 A1 | 11/2018 |
| WO | 2019/073004 A1 | 4/2019 |
| WO | 2019/162370 A1 | 8/2019 |
| WO | WO-2020/039177 A1 | 2/2020 |
| WO | WO-2020/039179 A1 | 2/2020 |

OTHER PUBLICATIONS

International Search Report and Written Opinion for PCT/US2020/045590 dated Dec. 14, 2020.

International Search Report and Written Opinion for PCT/US2020/045691 dated Jan. 12, 2021.

International Search Report and Written Opinion for PCT/US2020/045588 dated Feb. 2, 2021.

Invitation to Pay Additional Fees for PCT/EP2020/083536 dated Mar. 1, 2021.

Invitation to Pay Additional Fees for PCT/EP2020/083539 dated Mar. 2, 2021.

(56) References Cited

OTHER PUBLICATIONS

Invitation to Pay Additional Fees for PCT/EP2020/083551 dated Mar. 2, 2021.
Invitation to Pay Additional Fees for PCT/EP2020/083549 dated Mar. 2, 2021.
International Search Report and Written Opinion for corresponding International application No. PCT/EP2020/083536 dated Jun. 11, 2021.
International Search Report and Written Opinion for corresponding International application No. PCT/EP2020/083549 dated Jun. 11, 2021.
International Search Report and Written Opinion for corresponding International application No. PCT/EP2020/083539 dated Jun. 11, 2021.
International Search Report and Written Opinion for corresponding International application No. PCT/EP2020/083551 dated Jun. 11, 2021.
Office Action for U.S. Appl. No. 16/695,515 dated Jul. 28, 2021.
Office Action for U.S. Appl. No. 16/695,643 dated Sep. 1, 2021.
Office Action for U.S. Appl. No. 16/695,692 dated Sep. 22, 2021.
Office Action for U.S. Appl. No. 16/696,189 dated Oct. 14, 2021.
Written Opinion for PCT/EP2020/083549 dated Oct. 15, 2021.
Written Opinion for PCT/EP2020/083536 dated Oct. 12, 2021.
Written Opinion for PCT/EP2020/083539 dated Oct. 14, 2021.
Invitation to Pay Fees for PCT/EP2020/083551 dated Oct. 14, 2021.
Office Action for U.S. Appl. No. 16/696,007 dated Nov. 3, 2021.
Office action dated Nov. 10, 2021, issued in corresponding U.S. Appl. No. 16/696,081.
Written Opinion for corresponding International application No. PCT/EP2020/083551 dated Nov. 19, 2021.
Notice of Allowance for U.S. Appl. No. 16/695,643 dated Dec. 20, 2021.
Notice of Allowance for U.S. Appl. No. 16/695,692 dated Jan. 4, 2022.
Office Action for U.S. Appl. No. 16/696,189 dated Jan. 10, 2022.
Notice of Allowance for U.S. Appl. No. 16/696,007 dated Jan. 28, 2022.
Notice of Allowance for U.S. Appl. No. 16/695,515 dated Feb. 1, 2022.
Notice of Allowance for U.S. Appl. No. 16/696,007 dated Mar. 7, 2022.
Notice of Allowance for U.S. Appl. No. 16/696,081 dated Mar. 15, 2022.
Notice of Allowance for U.S. Appl. No. 16/696,189 dated Mar. 10, 2022.
Notice of Allowance for U.S. Appl. No. 16/695,692 dated Mar. 21, 2022.
International Preliminary Report on Patentability for PCT/EP2020/083536 dated Feb. 23, 2022.
Notice of Allowance for U.S. Appl. No. 16/695,643 dated Mar. 24, 2022.
Notice of Allowance for U.S. Appl. No. 16/696,189 dated Mar. 28, 2022.
International Preliminary Report on Patentability for PCT/EP2020/083539 dated Feb. 24, 2022.
International Preliminary Report on Patentability for PCT/EP2020/083551 dated Feb. 24, 2022.
International Preliminary Report on Patentability for PCT/EP2020/083549 dated Feb. 24, 2022.
Office Action for U.S. Appl. No. 16/695,415 dated Mar. 29, 2022.
Office Action for U.S. Appl. No. 16/695,563 dated Mar. 30, 2022.
Office Action for U.S. Appl. No. 16/695,643 dated Apr. 22, 2022.
Notice of Allowance for U.S. Appl. No. 16/695,692 dated Apr. 25, 2022.
Notice of Allowance for U.S. Appl. No. 16/696,007 dated Apr. 28, 2022.
Notice of Allowance for U.S. Appl. No. 16/696,189 dated May 5, 2022.
Notice of Allowance for U.S. Appl. No. 16/696,081 dated May 4, 2022.
Office Action for U.S. Appl. No. 16/695,515 dated May 27, 2022.
International Preliminary Report on Patentability for PCT/US2020/045590 dated Jun. 9, 2022.
International Preliminary Report on Patentability for PCT/US2020/045692 dated Jun. 9, 2022.
International Preliminary Report on Patentability for PCT/US2020/045588 dated Jun. 9, 2022.
International Preliminary Report on Patentability for PCT/US2020/045691 dated Jun. 9, 2022.
Notice of Allowance for corresponding U.S. Appl. No. 16/695,692 dated Jul. 13, 2022.
Notice of Allowance for U.S. Appl. No. 16/696,007 dated Jul. 18, 2022.
Notice of Allowance for U.S. Appl. No. 16/695,415 dated Jul. 25, 2022.
Notice of Allowance for U.S. Appl. No. 16/695,563 dated Jul. 22, 2022.
Notice of Allowance for U.S. Appl. No. 16/696,189 dated Jul. 27, 2022.
Notice of Allowance for U.S. Appl. No. 16/696,081 dated Jul. 29, 2022.
Notice of Allowance dated Oct. 25, 2022 issued in corresponding U.S. Appl. No. 16/695,643.
Notice of Allowance dated Nov. 17, 2022 issued in related U.S. Appl. No. 16/695,515.
Office Action dated Feb. 12, 2024 issued in corresponding U.S. Appl. No. 18/161,255.
Office Action dated Feb. 13, 2024 issued in corresponding U.S. Appl. No. 18/167,555.
Office Action dated Feb. 13, 2024 issued in corresponding U.S. Appl. No. 18/068,273.
Office Action dated Jan. 16, 2024 issued in related U.S. Appl. No. 18/051,222.
Office Action dated Nov. 14, 2023 in corresponding Brazilian patent application No. 1120220100329.
Office Action dated Jan. 30, 2024 issued in corresponding U.S. Appl. No. 18/053,074.
Office Action dated Feb. 5, 2024 issued in corresponding U.S. Appl. No. 18/067,947.
Office Action dated Jan. 31, 2024 issued in corresponding U.S. Appl. No. 18/055,124.
Notice of Allowance and Search Report dated Mar. 20, 2024 issued in Russian patent application No. 2022116872.
Office Action dated Aug. 6, 2024 issued in Japanese patent application No. 2021-570817.
Office Action dated Aug. 6, 2024 issued in Japanese patent application No. 2021-570816.
Notice of Allowance dated Sep. 19, 2024 issued in U.S. Appl. No. 18/161,255.
Notice of Allowance dated Sep. 23, 2024 issued in U.S. Appl. No. 18/068,273.
Notice of Allowance dated Sep. 19, 2024 issued in U.S. Appl. No. 18/053,074.
Notice of Allowance dated Sep. 20, 2024 issued in U.S. Appl. No. 18/055,124.
Notice of Allowance dated Sep. 26, 2024 issued in U.S. Appl. No. 18/051,222.
Notice of Allowance dated Oct. 10, 2024 issued in U.S. Appl. No. 18/067,947.
Notice of Allowance dated Oct. 11, 2024 issued in U.S. Appl. No. 18/167,555.
Office Action dated Sep. 27, 2024 issued in Mexican Patent Application No. MX/a/2021/014641.

* cited by examiner

NON-NICOTINE POD ASSEMBLIES AND NON-NICOTINE E-VAPING DEVICES

CROSS-REFERENCE TO RELATED APPLICATION

This application claims priority under 35 U.S.C. § 120 to U.S. application Ser. No. 16/695,515, filed Nov. 26, 2019, the entire contents of which are incorporated herein by reference.

BACKGROUND

Field

The present disclosure relates to non-nicotine electronic vaping (e-vaping) devices.

Description of Related Art

Some non-nicotine e-vaping devices include a first section coupled to a second section. The first section may include a wick and a heater. The wick is configured to move a non-nicotine pre-vapor formulation via capillary action and is positioned so as to extend into a reservoir and a vapor passage. The heater is in thermal contact with the wick and is configured to vaporize the non-nicotine pre-vapor formulation drawn via the wick into the vapor passage. The second section includes a power source configured to supply an electric current to the heater during vaping. The initiation of the operation of the non-nicotine e-vaping device may be achieved through manual- and/or puff-activation.

SUMMARY

At least one embodiment relates to a non-nicotine e-vaping device.

In an example embodiment, a non-nicotine e-vaping device may include a non-nicotine pod assembly and a device body. The non-nicotine pod assembly has an upstream end and a downstream end and is configured to hold a non-nicotine pre-vapor formulation. The upstream end may define at least one upstream recess, and the downstream end may define at least one downstream recess. The device body defines a through hole configured to receive the non-nicotine pod assembly. The through hole includes an upstream sidewall and a downstream sidewall. The upstream sidewall may include at least one upstream protrusion, and the downstream sidewall may include at least one downstream protrusion. The at least one upstream protrusion and the at least one downstream protrusion may be configured to engage with the at least one upstream recess and the at least one downstream recess, respectively, so as to retain the non-nicotine pod assembly within the through hole of the device body.

At least one embodiment relates to a device body for a non-nicotine e-vaping device.

In an example embodiment, a device body may include a device housing defining a through hole configured to receive a non-nicotine pod assembly. The through hole includes an upstream sidewall and a downstream sidewall. The upstream sidewall includes at least one upstream protrusion, and the downstream sidewall includes at least one downstream protrusion. The at least one upstream protrusion is configured to engage with at least one upstream recess of the non-nicotine pod assembly so as to facilitate a pivoting of the non-nicotine pod assembly into the through hole.

At least one embodiment relates to a non-nicotine pod assembly for a non-nicotine e-vaping device.

In an example embodiment, a non-nicotine pod assembly may include a pod body configured to hold a non-nicotine pre-vapor formulation. The pod body has an upstream end and a downstream end. The upstream end may define a pod inlet and at least one upstream recess. The downstream end may define a pod outlet and at least one downstream recess.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
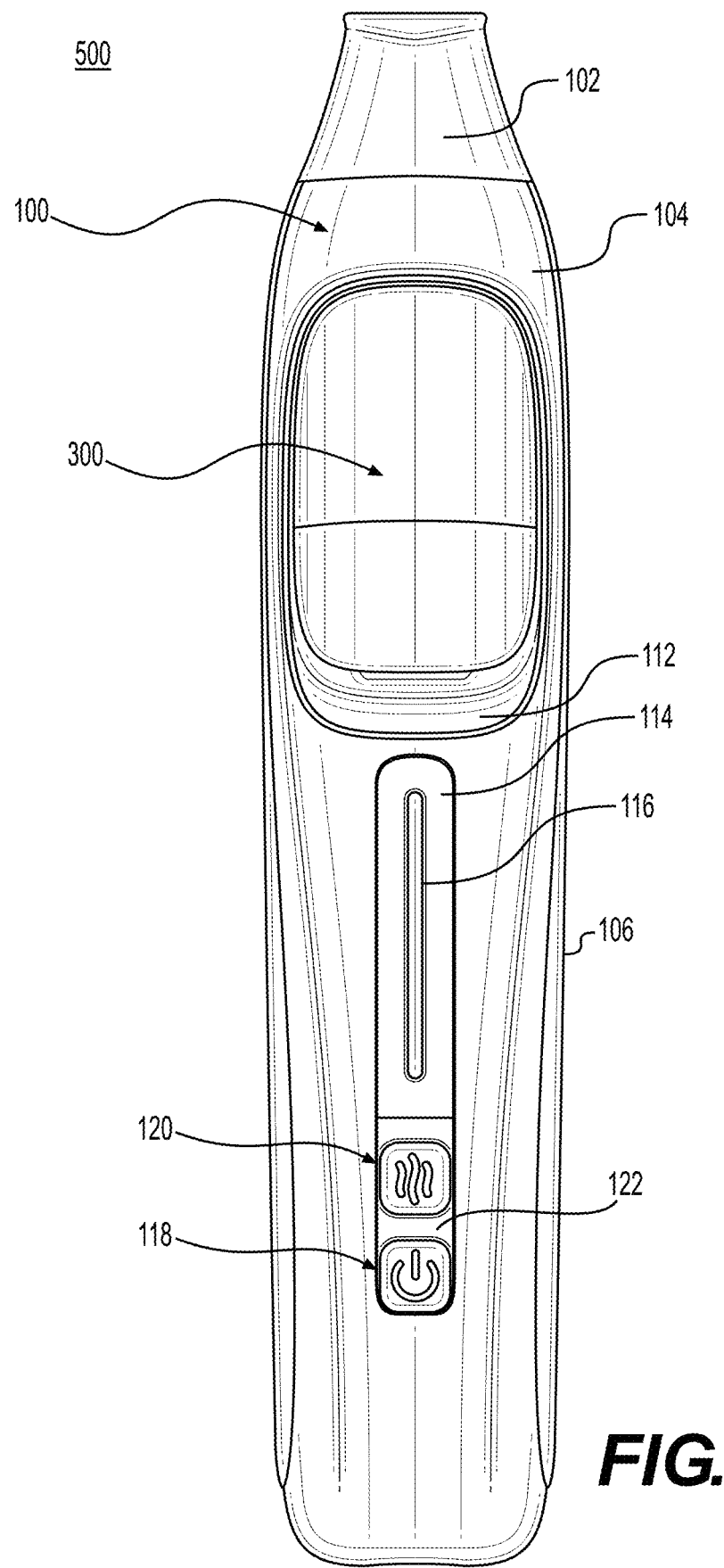
FIG. 1 is a front view of a non-nicotine e-vaping device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," "covering," etc. another element or layer, it may be directly on, connected to, coupled to, attached to, adjacent to, covering, etc. the other element or layer or intervening elements or layers may be present. In contrast, when an element is referred to as being "directly on," "directly connected to," "directly coupled to," etc. another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the term "same" or "identical" is used in the description of example embodiments, it should be understood that some imprecisions may exist. Thus, when one element or value is referred to as being the same as another element or value, it should be understood that the element or value is the same as the other element or value within a manufacturing or operational tolerance range (e.g., ±10%).

When the terms "about" or "substantially" are used in connection with a numerical value, it should be understood that the associated numerical value includes a manufacturing or operational tolerance (e.g., ±10%) around the stated numerical value. Moreover, when the words "generally" and "substantially" are used in connection with a geometric shape, it should be understood that the precision of the geometric shape is not required but that latitude for the shape is within the scope of the disclosure.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 2:
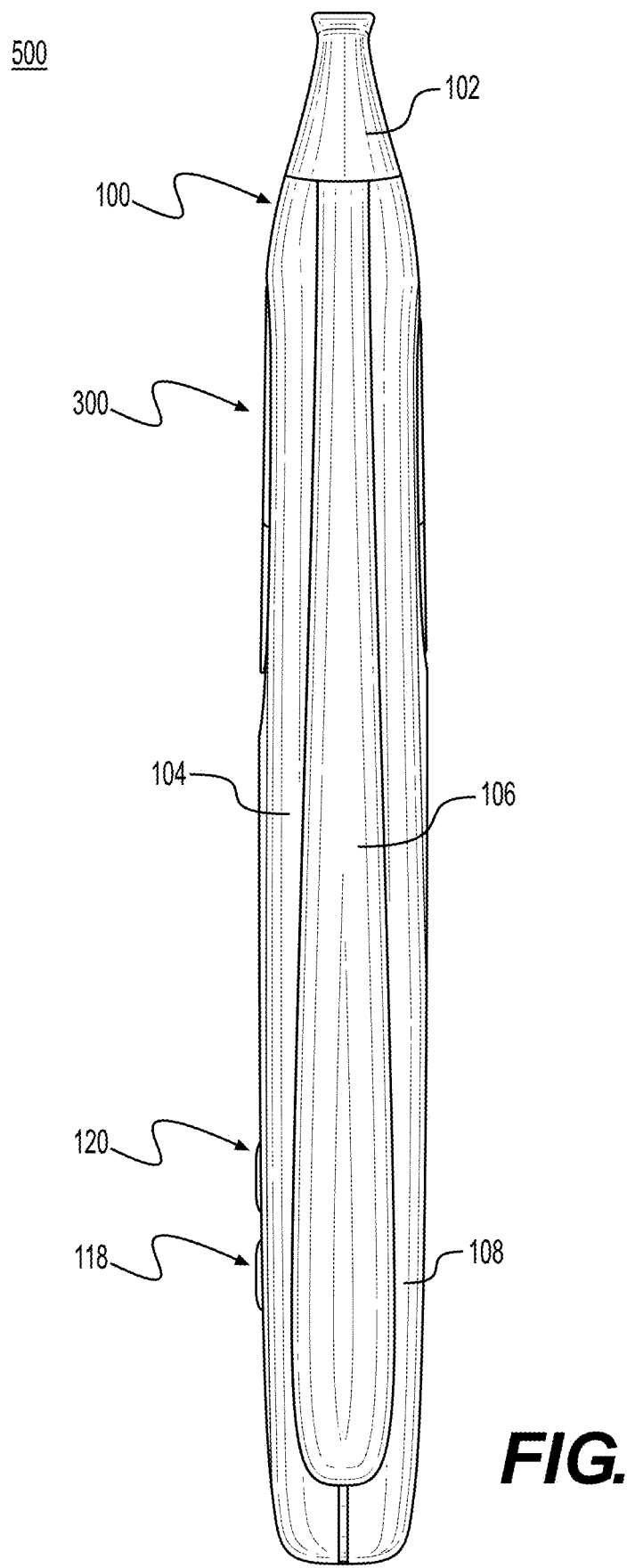
FIG. 2 is a side view of the non-nicotine e-vaping device of FIG. 1.
Figure 3:
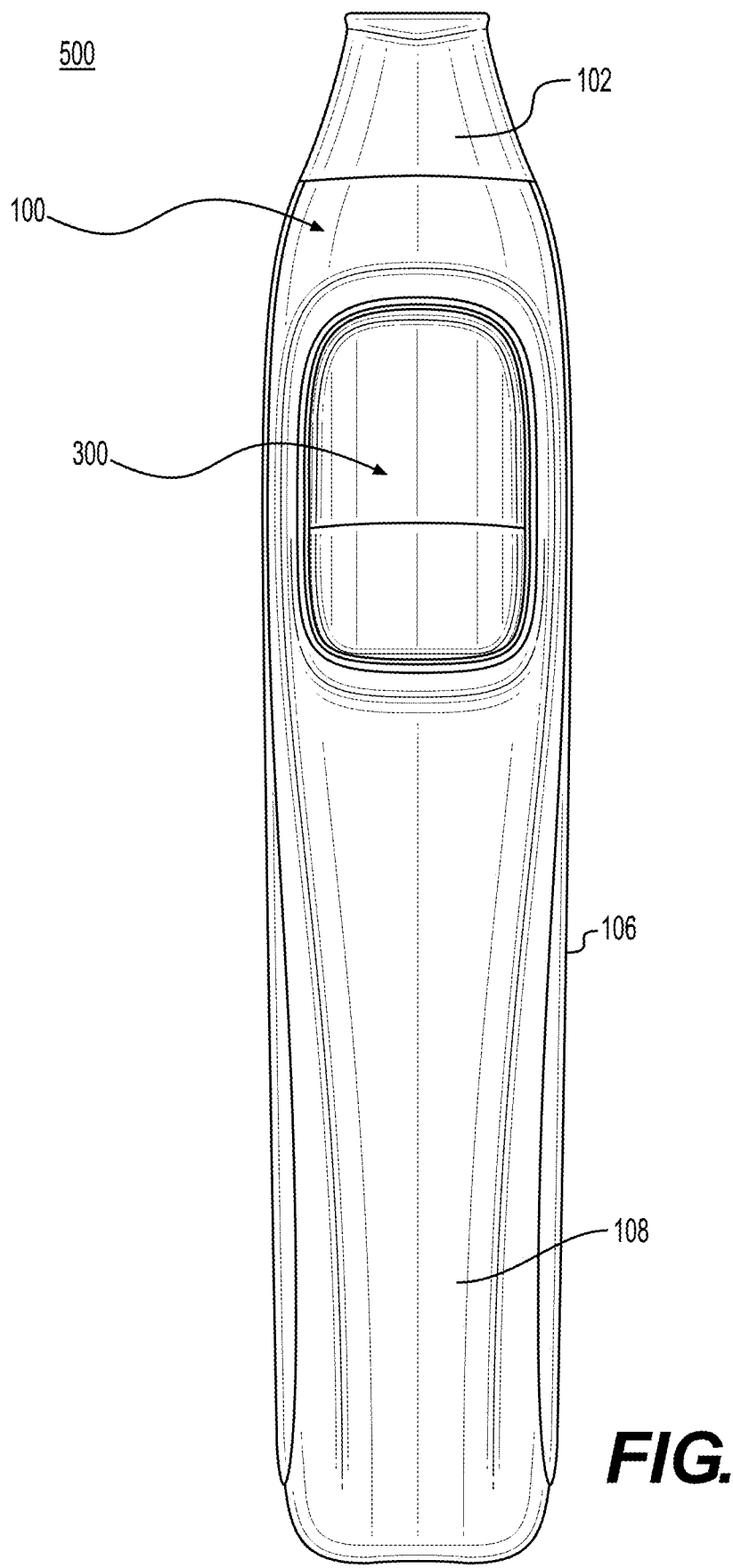
FIG. 3 is a rear view of the non-nicotine e-vaping device of FIG. 1.

FIG. 1 is a front view of a non-nicotine e-vaping device according to an example embodiment. FIG. 2 is a side view of the non-nicotine e-vaping device of FIG. 1. FIG. 3 is a rear view of the non-nicotine e-vaping device of FIG. 1. Referring to FIGS. 1-3, a non-nicotine e-vaping device 500 includes a device body 100 that is configured to receive a non-nicotine pod assembly 300. The non-nicotine pod assembly 300 is a modular article configured to hold a non-nicotine pre-vapor formulation. A non-nicotine pre-vapor formulation is a material or combination of materials that is devoid of nicotine and that may be transformed into a non-nicotine vapor. For example, the non-nicotine pre-vapor formulation may include a liquid, solid, and/or gel formulation. These may include, for example and without limitation, solutions and suspensions (e.g., emulsions) containing water, oil, beads, solvents, active ingredients, ethanol, plant extracts, non-nicotine compounds, natural or artificial flavors, vapor formers such as glycerin and propylene glycol, and/or any other ingredients that may be suitable for vaping. During vaping, the non-nicotine e-vaping device 500 is configured to heat the non-nicotine pre-vapor formulation to generate a non-nicotine vapor. Non-nicotine vapor, non-nicotine aerosol, and non-nicotine dispersion are used interchangeably and refer to the matter generated or outputted by the devices disclosed, claimed, and/or equivalents thereof, wherein such matter is devoid of nicotine.

As shown in FIGS. 1 and 3, the non-nicotine e-vaping device 500 extends in a longitudinal direction and has a length that is greater than its width. In addition, as shown in FIG. 2, the length of the non-nicotine e-vaping device 500 is also greater than its thickness. Furthermore, the width of the non-nicotine e-vaping device 500 may be greater than its thickness. Assuming an x-y-z Cartesian coordinate system, the length of the non-nicotine e-vaping device 500 may be measured in the y-direction, the width may be measured in the x-direction, and the thickness may be measured in the z-direction. The non-nicotine e-vaping device 500 may have a substantially linear form with tapered ends based on its front, side, and rear views, although example embodiments are not limited thereto.

The device body 100 includes a front cover 104, a frame 106, and a rear cover 108. The front cover 104, the frame 106, and the rear cover 108 form a device housing that encloses mechanical components, electronic components, and/or circuitry associated with the operation of the non-nicotine e-vaping device 500. For instance, the device housing of the device body 100 may enclose a power source configured to power the non-nicotine e-vaping device 500, which may include supplying an electric current to the non-nicotine pod assembly 300. In addition, when assembled, the front cover 104, the frame 106, and the rear cover 108 may constitute a majority of the visible portion of the device body 100. The device housing may be regarded as including all constituent parts of the device body 100 except for the mouthpiece 102. Stated differently, the mouthpiece 102 and the device housing may be regarded as forming the device body 100.

The front cover 104 (e.g., first cover) defines a primary opening configured to accommodate a bezel structure 112. The primary opening may have a rounded rectangular shape, although other shapes are possible depending on the shape of the bezel structure 112. The bezel structure 112 defines a through hole 150 configured to receive the non-nicotine pod assembly 300. The through hole 150 is discussed herein in more detail in connection with, for instance, FIG. 9.

The front cover 104 also defines a secondary opening configured to accommodate a light guide arrangement. The secondary opening may resemble a slot, although other shapes are possible depending on the shape of the light guide arrangement. In an example embodiment, the light guide arrangement includes a light guide housing 114 and a button housing 122. The light guide housing 114 is configured to expose a light guide lens 116, while the button housing 122 is configured to expose a first button lens 124 and a second button lens 126 (e.g., FIG. 16). The first button lens 124 and an upstream portion of the button housing 122 may form a first button 118. Similarly, the second button lens 126 and a downstream portion of the button housing 122 may form a second button 120. The button housing 122 may be in a form of a single structure or two separate structures. With the latter form, the first button 118 and the second button 120 can move with a more independent feel when pressed.

The operation of the non-nicotine e-vaping device 500 may be controlled by the first button 118 and the second button 120. For instance, the first button 118 may be a power button, and the second button 120 may be an intensity button. Although two buttons are shown in the drawings in connection with the light guide arrangement, it should be understood that more (or less) buttons may be provided depending on the available features and desired user interface.

The frame 106 (e.g., base frame) is the central support structure for the device body 100 (and the non-nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, "proximal" (and, conversely, "distal") is in relation to an adult vaper during vaping, and "downstream" (and, conversely, "upstream") is in relation to a flow of the non-nicotine vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the non-nicotine e-vaping device 500.

The rear cover 108 (e.g., second cover) also defines an opening configured to accommodate the bezel structure 112. The opening may have a rounded rectangular shape, although other shapes are possible depending on the shape of the bezel structure 112. In an example embodiment, the opening in the rear cover 108 is smaller than the primary opening in the front cover 104. In addition, although not shown, it should be understood that a light guide arrangement (e.g., including buttons) may be provided on the rear of the non-nicotine e-vaping device 500 in addition to (or in lieu of) the light guide arrangement on the front of the non-nicotine e-vaping device 500.

The front cover 104 and the rear cover 108 may be configured to engage with the frame 106 via a snap-fit arrangement. For instance, the front cover 104 and/or the rear cover 108 may include clips configured to interlock with corresponding mating members of the frame 106. In a non-limiting embodiment, the clips may be in a form of tabs with orifices configured to receive the corresponding mating members (e.g., protrusions with beveled edges) of the frame 106. Alternatively, the front cover 104 and/or the rear cover 108 may be configured to engage with the frame 106 via an interference fit (which may also be referred to as a press fit or friction fit). However, it should be understood that the front cover 104, the frame 106, and the rear cover 108 may be coupled via other suitable arrangements and techniques.

The device body 100 also includes a mouthpiece 102. The mouthpiece 102 may be secured to the proximal end of the frame 106. Additionally, as shown in FIG. 2, in an example embodiment where the frame 106 is sandwiched between the front cover 104 and the rear cover 108, the mouthpiece 102 may abut the front cover 104, the frame 106, and the rear cover 108. Furthermore, in a non-limiting embodiment, the mouthpiece 102 may be joined with the device housing via a bayonet connection.

Figure 4:
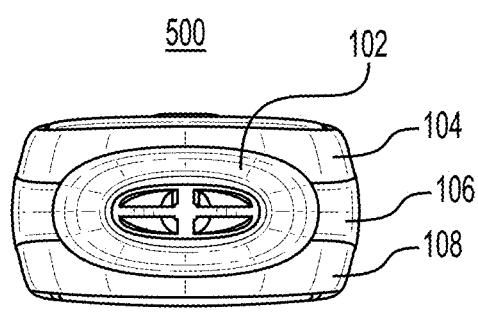
FIG. 4 is a proximal end view of the non-nicotine e-vaping device of FIG. 1.

FIG. 4 is a proximal end view of the non-nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped. In addition, the outlet face of the mouthpiece 102 may include a first crossbar corresponding to a major axis of the elliptically-shaped outlet face and a second crossbar corresponding to a minor axis of the elliptically-shaped outlet face. Furthermore, the first crossbar and the second crossbar may intersect perpendicularly and be integrally formed parts of the mouthpiece 102. Although the outlet face is shown as defining four vapor outlets, it should be understood that example embodiments are not limited thereto. For instance, the outlet face may define less than four (e.g., one, two) vapor outlets or more than four (e.g., six, eight) vapor outlets.

Figure 5:
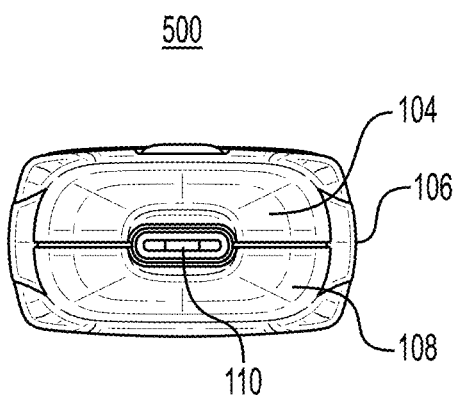
FIG. 5 is a distal end view of the non-nicotine e-vaping device of FIG. 1.

FIG. 5 is a distal end view of the non-nicotine e-vaping device of FIG. 1. Referring to FIG. 5, the distal end of the non-nicotine e-vaping device 500 includes a port 110. The port 110 is configured to receive an electric current (e.g., via a USB/mini-USB cable) from an external power source so as to charge an internal power source within the non-nicotine e-vaping device 500. In addition, the port 110 may also be configured to send data to and/or receive data (e.g., via a USB/mini-USB cable) from another non-nicotine e-vaping device or other electronic device (e.g., phone, tablet, computer). Furthermore, the non-nicotine e-vaping device 500 may be configured for wireless communication with another electronic device, such as a phone, via an application software (app) installed on that electronic device. In such an instance, an adult vaper may control or otherwise interface with the non-nicotine e-vaping device 500 (e.g., locate the non-nicotine e-vaping device, check usage information, change operating parameters) through the app.

Figure 6:
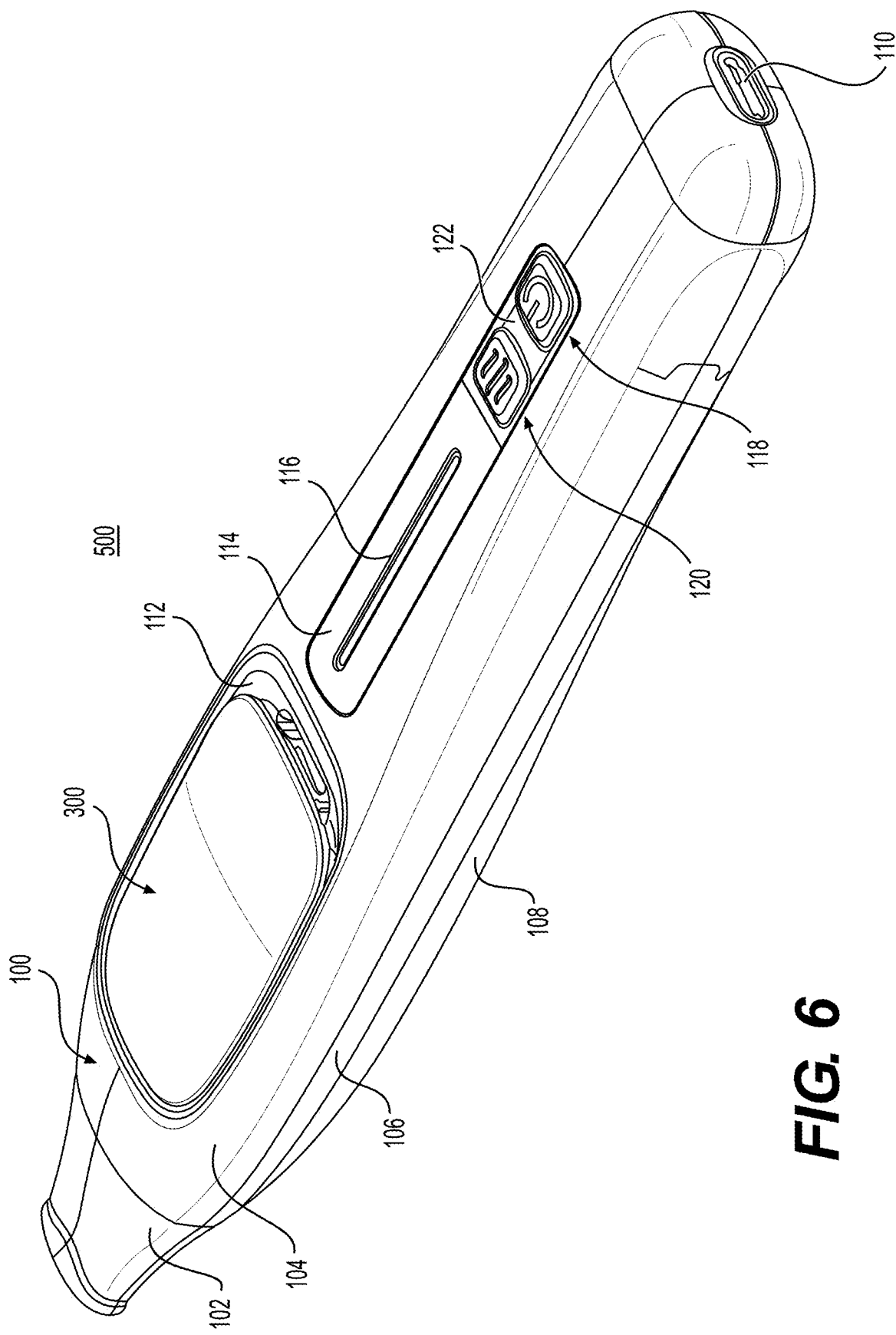
FIG. 6 is a perspective view of the non-nicotine e-vaping device of FIG. 1.
Figure 7:
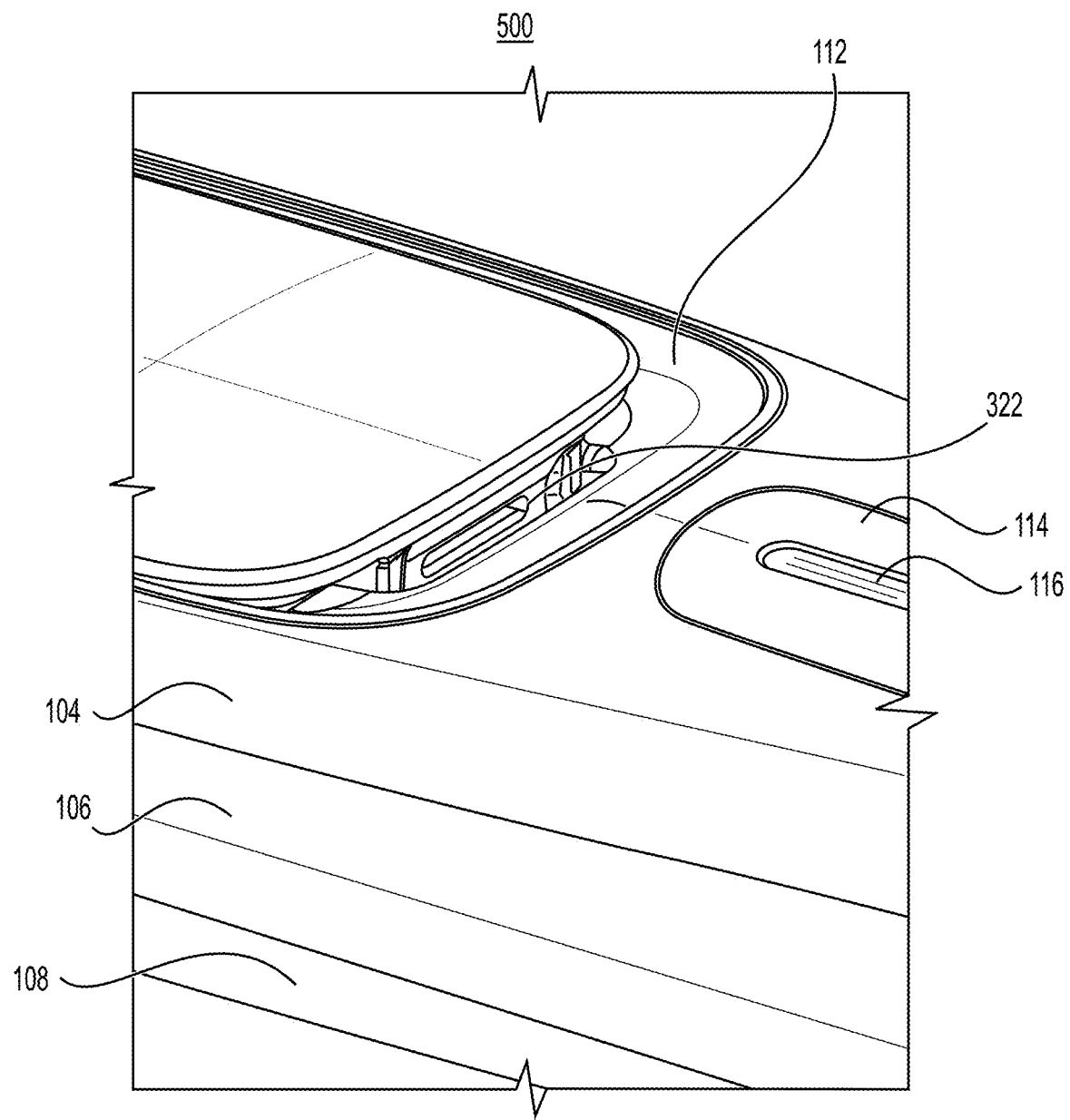
FIG. 7 is an enlarged view of the pod inlet in FIG. 6.

FIG. 6 is a perspective view of the non-nicotine e-vaping device of FIG. 1. FIG. 7 is an enlarged view of the pod inlet in FIG. 6. Referring to FIGS. 6-7, and as briefly noted above, the non-nicotine e-vaping device 500 includes a non-nicotine pod assembly 300 configured to hold a non-nicotine pre-vapor formulation. The non-nicotine pod assembly 300 has an upstream end (which faces the light guide arrangement) and a downstream end (which faces the mouthpiece 102). In a non-limiting embodiment, the upstream end is an opposing surface of the non-nicotine pod assembly 300 from the downstream end. The upstream end of the non-nicotine pod assembly 300 defines a pod inlet 322. The device body 100 defines a through hole (e.g., through hole 150 in FIG. 9) configured to receive the non-nicotine pod assembly 300. In an example embodiment, the bezel structure 112 of the device body 100 defines the through hole and includes an upstream rim. As shown, particularly in FIG. 7, the upstream rim of the bezel structure 112 is angled (e.g., dips inward) so as to expose the pod inlet 322 when the non-nicotine pod assembly 300 is seated within the through hole of the device body 100.

For instance, rather than following the contour of the front cover 104 (so as to be relatively flush with the front face of the non-nicotine pod assembly 300 and, thus, obscure the pod inlet 322), the upstream rim of the bezel structure 112 is in a form of a scoop configured to direct ambient air into the pod inlet 322. This angled/scoop configuration (e.g., which may be curved) may help reduce or prevent the blockage of the air inlet (e.g., pod inlet 322) of the non-nicotine e-vaping device 500. The depth of the scoop may be such that less than half (e.g., less than a quarter) of the upstream end face of the non-nicotine pod assembly 300 is exposed. Additionally, in a non-limiting embodiment, the pod inlet 322 is in a form of a slot. Furthermore, if the device body 100 is regarded as extending in a first direction, then the slot may be regarded as extending in a second direction, wherein the second direction is transverse to the first direction.

Figure 8:
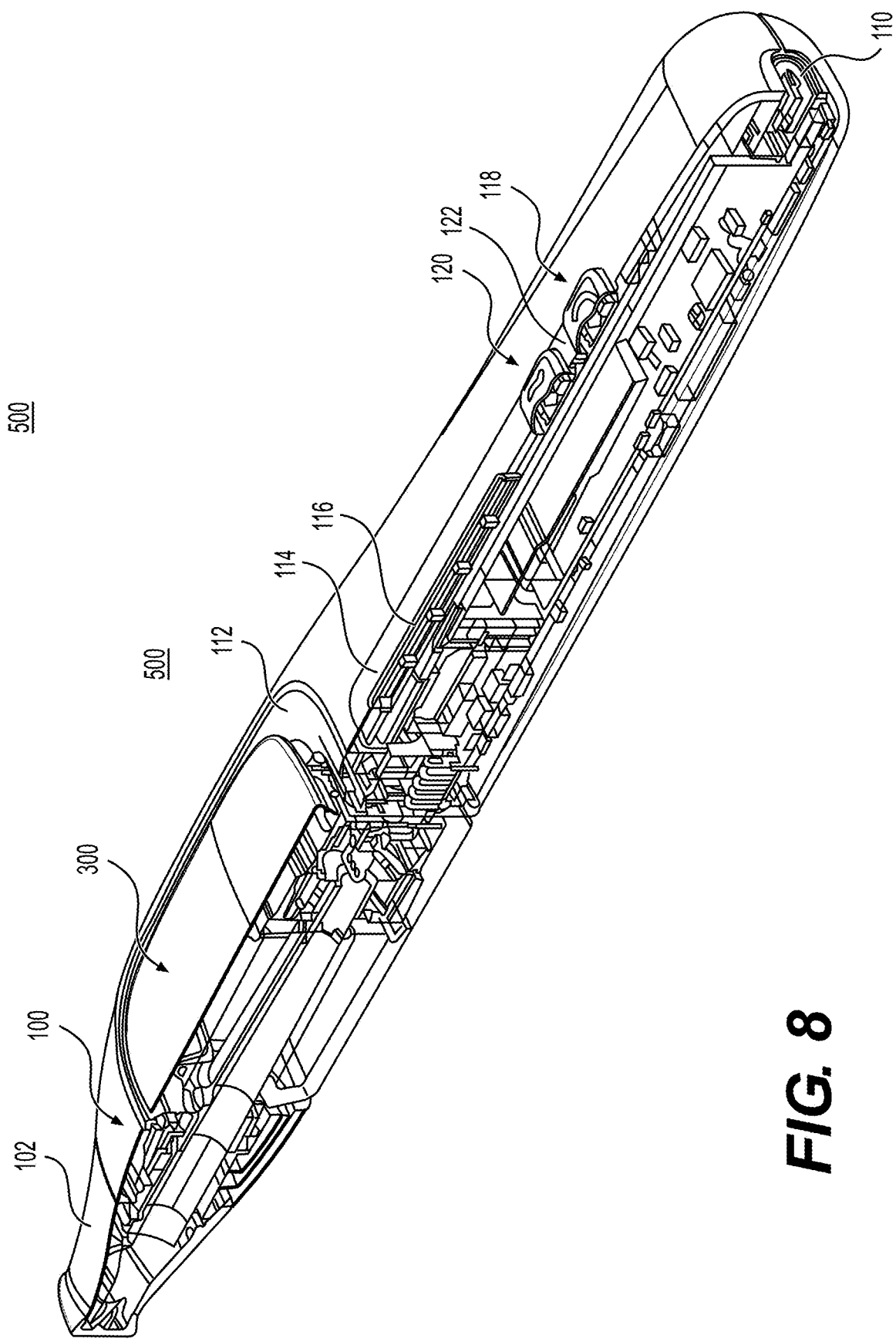
FIG. 8 is a cross-sectional view of the non-nicotine e-vaping device of FIG. 6.

FIG. 8 is a cross-sectional view of the non-nicotine e-vaping device of FIG. 6. In FIG. 8, the cross-section is taken along the longitudinal axis of the non-nicotine e-vaping device 500. As shown, the device body 100 and the non-nicotine pod assembly 300 include mechanical components, electronic components, and/or circuitry associated with the operation of the non-nicotine e-vaping device 500, which are discussed in more detail herein and/or are incorporated by reference herein. For instance, the non-nicotine pod assembly 300 may include mechanical components configured to actuate to release the non-nicotine pre-vapor formulation from a sealed reservoir within. The non-nicotine pod assembly 300 may also have mechanical aspects configured to engage with the device body 100 to facilitate the insertion and seating of the non-nicotine pod assembly 300.

Additionally, the non-nicotine pod assembly 300 may be a "smart pod" that includes electronic components and/or circuitry configured to store, receive, and/or transmit information to/from the device body 100. Such information may be used to authenticate the non-nicotine pod assembly 300 for use with the device body 100 (e.g., to prevent usage of an unapproved/counterfeit non-nicotine pod assembly). Furthermore, the information may be used to identify a type of the non-nicotine pod assembly 300 which is then correlated with a vaping profile based on the identified type. The vaping profile may be designed to set forth the general parameters for the heating of the non-nicotine pre-vapor formulation and may be subject to tuning, refining, or other adjustment by an adult vaper before and/or during vaping.

The non-nicotine pod assembly 300 may also communicate other information with the device body 100 that may be relevant to the operation of the non-nicotine e-vaping device 500. Examples of relevant information may include a level of the non-nicotine pre-vapor formulation within the non-nicotine pod assembly 300 and/or a length of time that has passed since the non-nicotine pod assembly 300 was inserted into the device body 100 and activated. For instance, if the non-nicotine pod assembly 300 was inserted into the device body 100 and activated more than a certain period of time prior (e.g., more than 6 months ago), the non-nicotine e-vaping device 500 may not permit vaping, and the adult vaper may be prompted to change to a new non-nicotine pod assembly even though the non-nicotine pod assembly 300 still contains adequate levels of non-nicotine pre-vapor formulation.

The device body 100 may include mechanical components (e.g., complementary structures) configured to engage, hold, and/or activate the non-nicotine pod assembly 300. In addition, the device body 100 may include electronic components and/or circuitry configured to receive an electric current to charge an internal power source (e.g., battery) which, in turn, is configured to supply power to the non-nicotine pod assembly 300 during vaping. Furthermore, the device body 100 may include electronic components and/or circuitry configured to communicate with the non-nicotine pod assembly 300, a different non-nicotine e-vaping device, other electronic devices (e.g., phone, tablet, computer), and/or the adult vaper. The information being communicated may include pod-specific data, current vaping details, and/or past vaping patterns/history. The adult vaper may be notified of such communications with feedback that is haptic (e.g., vibrations), auditory (e.g., beeps), and/or visual (e.g., colored/blinking lights). The charging and/or communication of information may be performed with the port 110 (e.g., via a USB/mini-USB cable).

Figure 9:
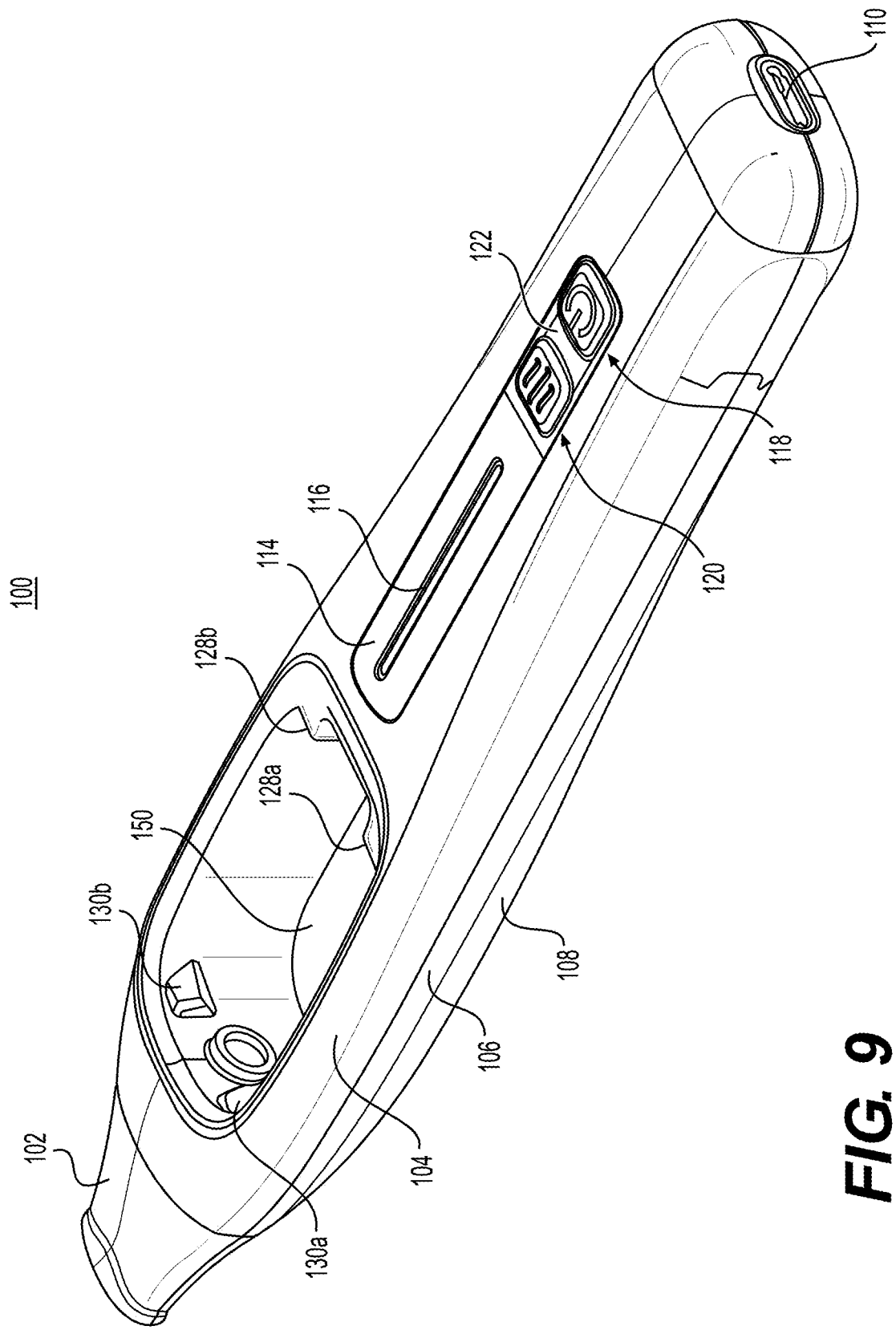
FIG. 9 is a perspective view of the device body of the non-nicotine e-vaping device of FIG. 6.

FIG. 9 is a perspective view of the device body of the non-nicotine e-vaping device of FIG. 6. Referring to FIG. 9, the bezel structure 112 of the device body 100 defines a through hole 150. The through hole 150 is configured to receive a non-nicotine pod assembly 300. To facilitate the insertion and seating of the non-nicotine pod assembly 300 within the through hole 150, the upstream rim of the bezel structure 112 includes a first upstream protrusion 128a and a second upstream protrusion 128b. The through hole 150 may have a rectangular shape with rounded corners. In an example embodiment, the first upstream protrusion 128a and the second upstream protrusion 128b are integrally formed with the bezel structure 112 and located at the two rounded corners of the upstream rim.

The downstream sidewall of the bezel structure 112 may define a first downstream opening, a second downstream opening, and a third downstream opening. A retention structure including a first downstream protrusion 130a and a second downstream protrusion 130b is engaged with the bezel structure 112 such that the first downstream protrusion 130a and the second downstream protrusion 130b protrude through the first downstream opening and the second downstream opening, respectively, of the bezel structure 112 and into the through hole 150. In addition, a distal end of the mouthpiece 102 extends through the third downstream opening of the bezel structure 112 and into the through hole 150 so as to be between the first downstream protrusion 130a and the second downstream protrusion 130b.

Figure 10:
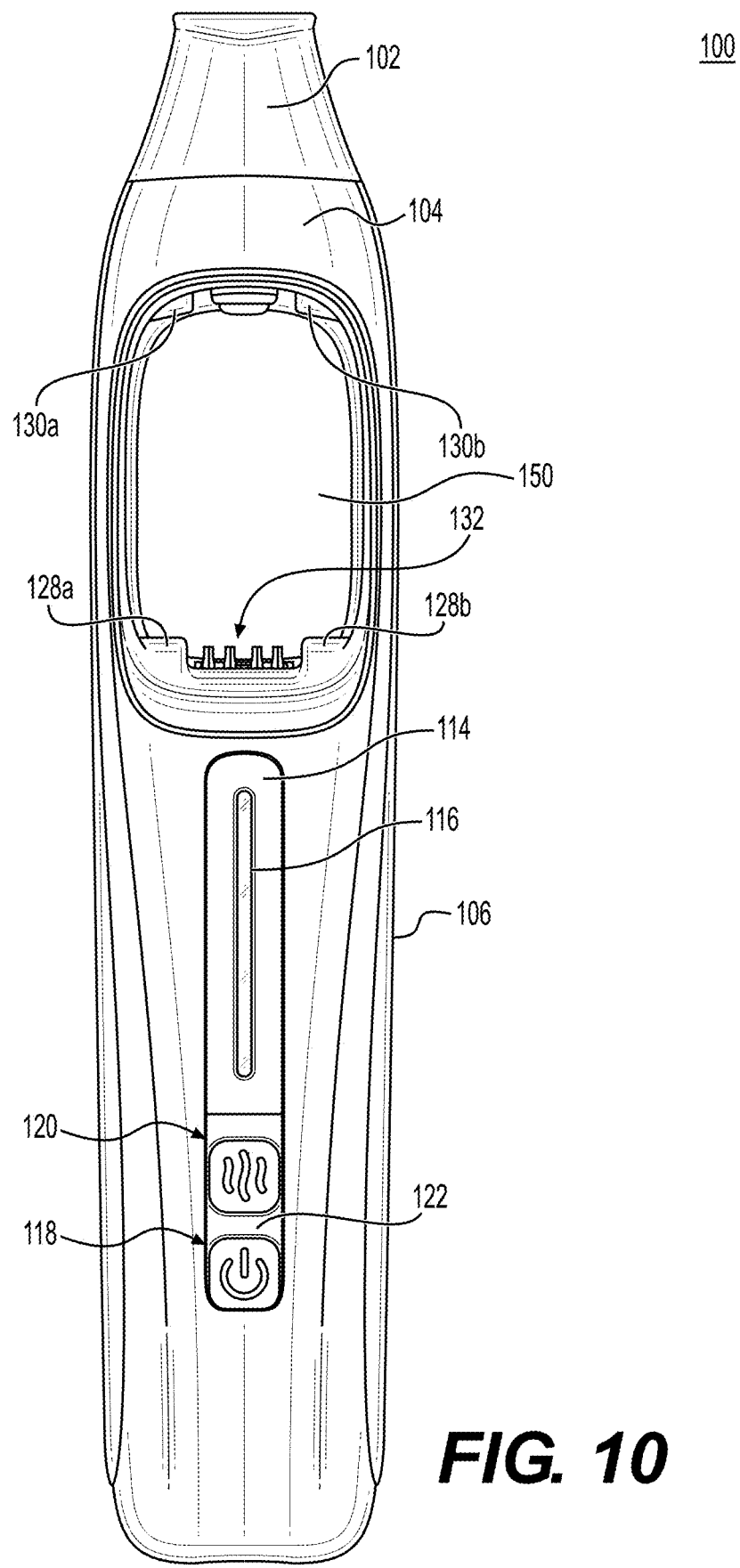
FIG. 10 is a front view of the device body of FIG. 9.

FIG. 10 is a front view of the device body of FIG. 9. Referring to FIG. 10, the device body 100 includes a device electrical connector 132 disposed at an upstream side of the through hole 150. The device electrical connector 132 of the device body 100 is configured to electrically engage with a non-nicotine pod assembly 300 that is seated within the through hole 150. As a result, power can be supplied from the device body 100 to the non-nicotine pod assembly 300 via the device electrical connector 132 during vaping. In addition, data can be sent to and/or received from the device body 100 and the non-nicotine pod assembly 300 via the device electrical connector 132.

Figure 11:
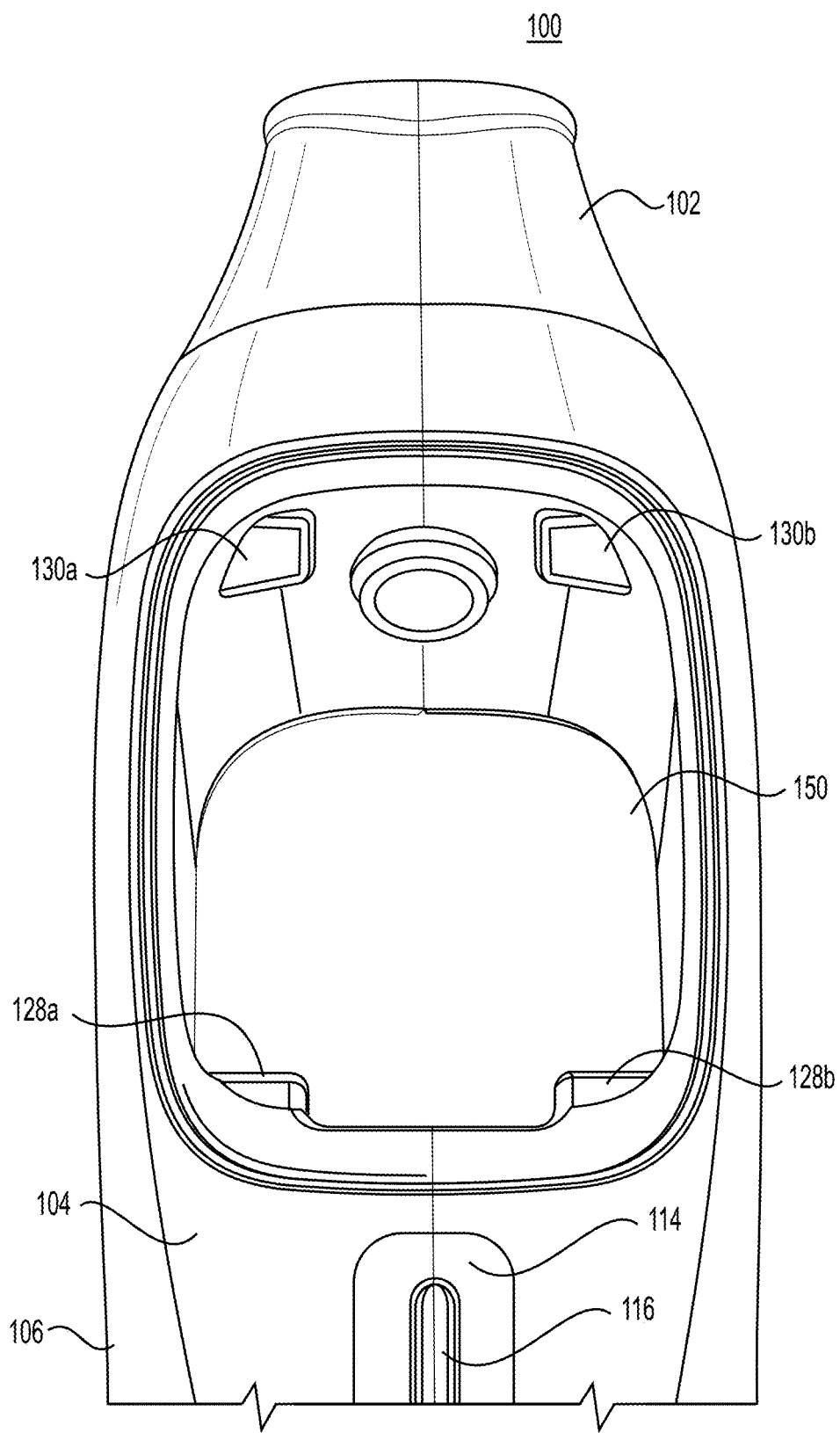
FIG. 11 is an enlarged perspective view of the through hole in FIG. 10.

FIG. 11 is an enlarged perspective view of the through hole in FIG. 10. Referring to FIG. 11, the first upstream protrusion 128a, the second upstream protrusion 128b, the first downstream protrusion 130a, the second downstream protrusion 130b, and the distal end of the mouthpiece 102 protrude into the through hole 150. In an example embodiment, the first upstream protrusion 128a and the second upstream protrusion 128b are stationary structures (e.g., stationary pivots), while the first downstream protrusion 130a and the second downstream protrusion 130b are tractable structures (e.g., retractable members). For instance, the first downstream protrusion 130a and the second downstream protrusion 130b may be configured (e.g., spring-loaded) to default to a protracted state while also configured to transition temporarily to a retracted state (and reversibly back to the protracted state) to facilitate an insertion of a non-nicotine pod assembly 300.

In particular, when inserting a non-nicotine pod assembly 300 into the through hole 150 of the device body 100, recesses at the upstream end face of the non-nicotine pod assembly 300 may be initially engaged with the first upstream protrusion 128a and the second upstream protrusion 128b followed by a pivoting of the non-nicotine pod assembly 300 (about the first upstream protrusion 128a and the second upstream protrusion 128b) until recesses at the downstream end face of the non-nicotine pod assembly 300 are engaged with the first downstream protrusion 130a and the second downstream protrusion 130b. In such an instance, the axis of rotation (during pivoting) of the non-nicotine pod assembly 300 may be orthogonal to the longitudinal axis of the device body 100. In addition, the first downstream protrusion 130a and the second downstream protrusion 130b, which may be biased so as to be tractable, may retract when the non-nicotine pod assembly 300 is being pivoted into the through hole 150 and resiliently protract to engage recesses at the downstream end face of the non-nicotine pod assembly 300. Furthermore, the engagement of the first downstream protrusion 130a and the second downstream protrusion 130b with recesses at the downstream end face of the non-nicotine pod assembly 300 may produce a haptic and/or auditory feedback (e.g., audible click) to notify an adult vaper that the non-nicotine pod assembly 300 is properly seated in the through hole 150 of the device body 100.

Figure 12:
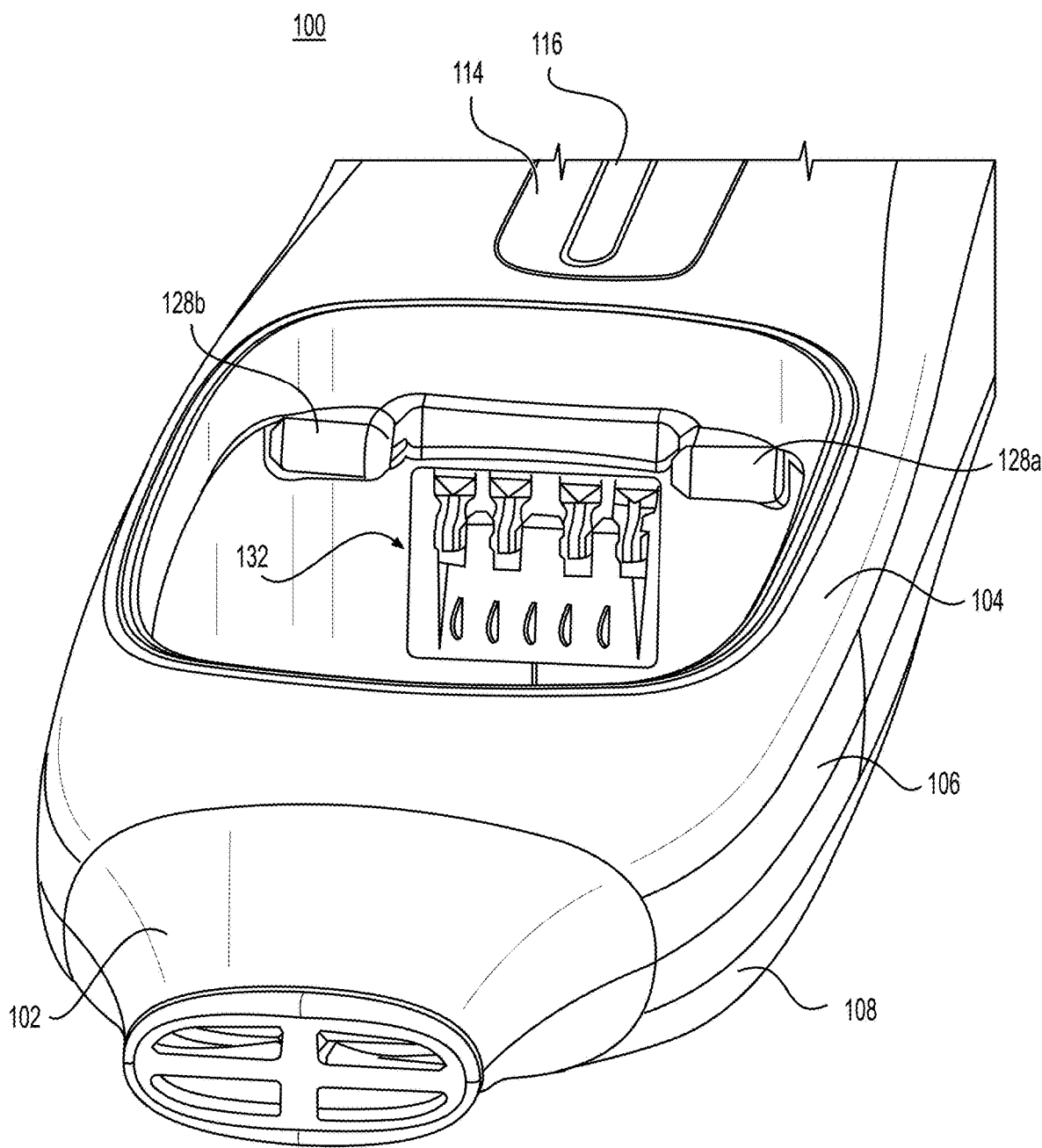
FIG. 12 is an enlarged perspective view of the device electrical contacts in FIG. 10.

FIG. 12 is an enlarged perspective view of the device electrical contacts in FIG. 10. The device electrical contacts of the device body 100 are configured to engage with the pod electrical contacts of the non-nicotine pod assembly 300 when the non-nicotine pod assembly 300 is seated within the through hole 150 of the device body 100. Referring to FIG. 12, the device electrical contacts of the device body 100 include the device electrical connector 132. The device electrical connector 132 includes power contacts and data contacts. The power contacts of the device electrical connector 132 are configured to supply power from the device body 100 to the non-nicotine pod assembly 300. As illustrated, the power contacts of the device electrical connector 132 include a first pair of power contacts and a second pair of power contacts (which are positioned so as to be closer to the front cover 104 than the rear cover 108). The first pair of power contacts (e.g., the pair adjacent to the first upstream protrusion 128a) may be a single integral structure that is distinct from the second pair of power contacts and that, when assembled, includes two projections that extend into the through hole 150. Similarly, the second pair of power contacts (e.g., the pair adjacent to the second upstream protrusion 128b) may be a single integral structure that is distinct from the first pair of power contacts and that, when assembled, includes two projections that extend into the through hole 150. The first pair of power contacts and the second pair of power contacts of the device electrical connector 132 may be tractably-mounted and biased so as to protract into the through hole 150 as a default and to retract (e.g., independently) from the through hole 150 when subjected to a force that overcomes the bias.

The data contacts of the device electrical connector 132 are configured to transmit data between a non-nicotine pod assembly 300 and the device body 100. As illustrated, the data contacts of the device electrical connector 132 include a row of five projections (which are positioned so as to be closer to the rear cover 108 than the front cover 104). The data contacts of the device electrical connector 132 may be distinct structures that, when assembled, extend into the through hole 150. The data contacts of the device electrical connector 132 may also be tractably-mounted and biased (e.g., with springs) so as to protract into the through hole 150 as a default and to retract (e.g., independently) from the through hole 150 when subjected to a force that overcomes the bias. For instance, when a non-nicotine pod assembly 300 is inserted into the through hole 150 of the device body 100, the pod electrical contacts of the non-nicotine pod assembly 300 will press against the corresponding device electrical contacts of the device body 100. As a result, the power contacts and the data contacts of the device electrical connector 132 will be retracted (e.g., at least partially retracted) into the device body 100 but will continue to push against the corresponding pod electrical contacts due to their resilient arrangement, thereby helping to ensure a proper electrical connection between the device body 100 and the non-nicotine pod assembly 300. Furthermore, such a connection may also be mechanically secure and have minimal contact resistance so as to allow power and/or signals between the device body 100 and the non-nicotine pod assembly 300 to be transferred and/or communicated reliably and accurately. While various aspects have been discussed in connection with the device electrical contacts of the device body 100, it should be understood that example embodiments are not limited thereto and that other configurations may be utilized.

Figure 13:
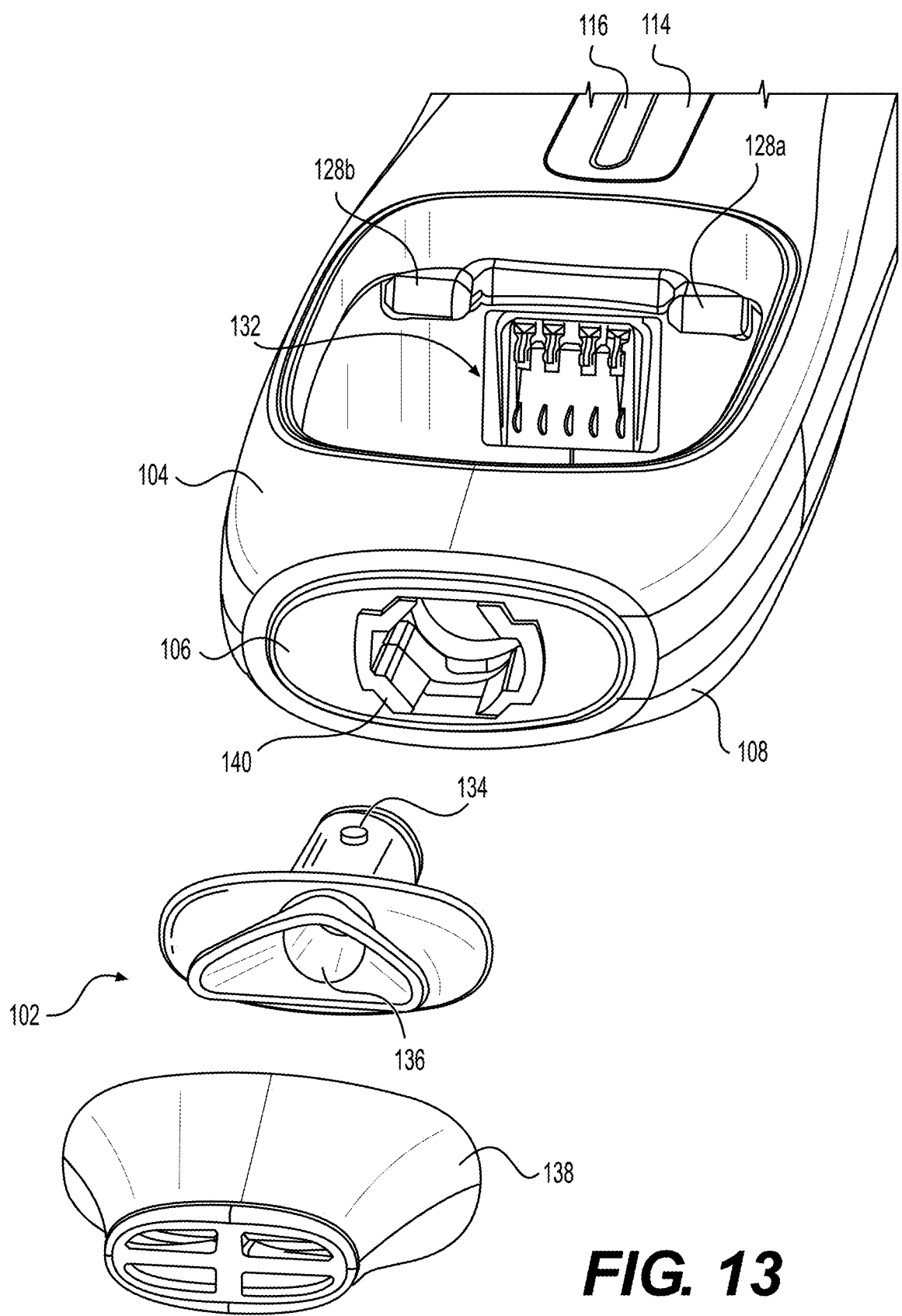
FIG. 13 is a partially exploded view involving the mouthpiece in FIG. 12.

FIG. 13 is a partially exploded view involving the mouthpiece in FIG. 12. Referring to FIG. 13, the mouthpiece 102 is configured to engage with the device housing via a retention structure 140. In an example embodiment, the retention structure 140 is situated so as to be primarily between the frame 106 and the bezel structure 112. As shown, the retention structure 140 is disposed within the device housing such that the proximal end of the retention structure 140 extends through the proximal end of the frame 106. The retention structure 140 may extend slightly beyond the proximal end of the frame 106 or be substantially even therewith. The proximal end of the retention structure 140 is configured to receive a distal end of the mouthpiece 102. The proximal end of the retention structure 140 may be a female end, while the distal end of the mouthpiece may be a male end.

For instance, the mouthpiece 102 may be coupled (e.g., reversibly coupled) to the retention structure 140 with a bayonet connection. In such an instance, the female end of the retention structure 140 may define a pair of opposing L-shaped slots, while the male end of the mouthpiece 102 may have opposing radial members 134 (e.g., radial pins) configured to engage with the L-shaped slots of the retention structure 140. Each of the L-shaped slots of the retention structure 140 may have a longitudinal portion and a circumferential portion. Optionally, the terminus of the circumferential portion may have a serif portion to help reduce or prevent the likelihood that that a radial member 134 of the mouthpiece 102 will inadvertently become disengaged. In a non-limiting embodiment, the longitudinal portions of the L-shaped slots extend in parallel and along a longitudinal axis of the device body 100, while the circumferential portions of the L-shaped slots extend around the longitudinal axis (e.g., central axis) of the device body 100. As a result, to couple the mouthpiece 102 to the device housing, the mouthpiece 102 shown in FIG. 13 is initially rotated 90 degrees to align the radial members 134 with the entrances to the longitudinal portions of the L-shaped slots of the retention structure 140. The mouthpiece 102 is then pushed into the retention structure 140 such that the radial members 134 slide along the longitudinal portions of the L-shaped slots until the junction with each of the circumferential portions is reached. At this point, the mouthpiece 102 is then rotated such that the radial members 134 travel across the circumferential portions until the terminus of each is reached. Where a serif portion is present at each terminus, a haptic and/or auditory feedback (e.g., audible click) may be produced to notify an adult vaper that the mouthpiece 102 has been properly coupled to the device housing.

The mouthpiece 102 defines a vapor passage 136 through which non-nicotine vapor flows during vaping. The vapor passage 136 is in fluidic communication with the through hole 150 (which is where the non-nicotine pod assembly 300 is seated within the device body 100). The proximal end of the vapor passage 136 may include a flared portion. In addition, the mouthpiece 102 may include an end cover 138. The end cover 138 may taper from its distal end to its proximal end. The outlet face of the end cover 138 defines a plurality of vapor outlets. Although four vapor outlets are shown in the end cover 138, it should be understood that example embodiments are not limited thereto.

Figure 14:
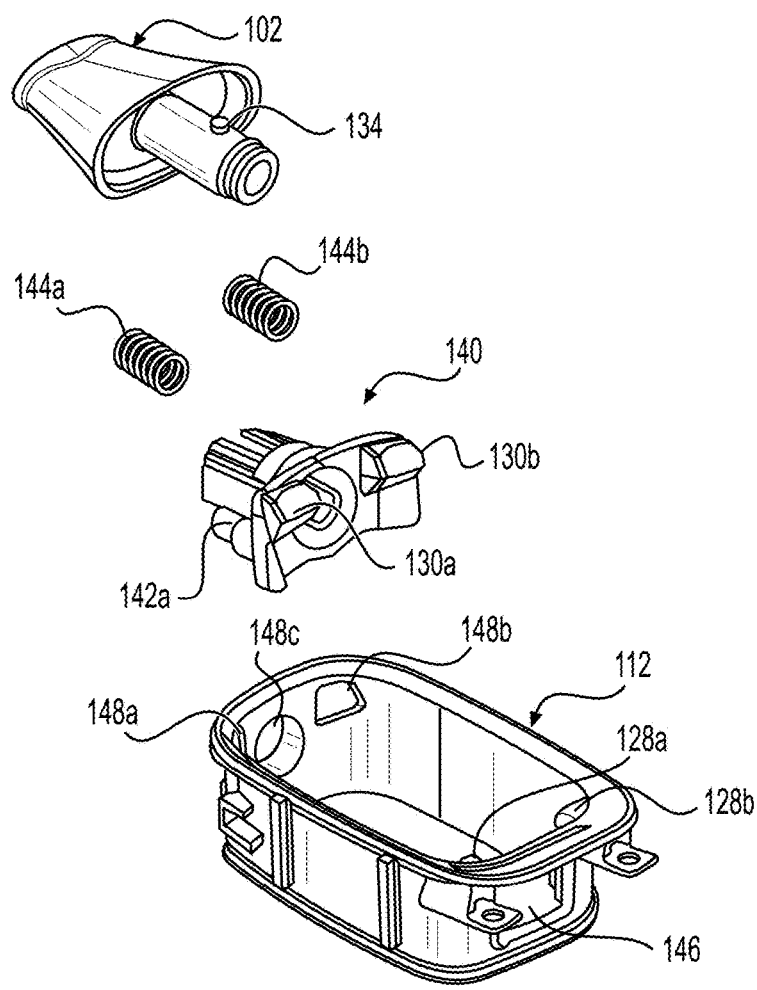
FIG. 14 is a partially exploded view involving the bezel structure in FIG. 9.
Figure 14:
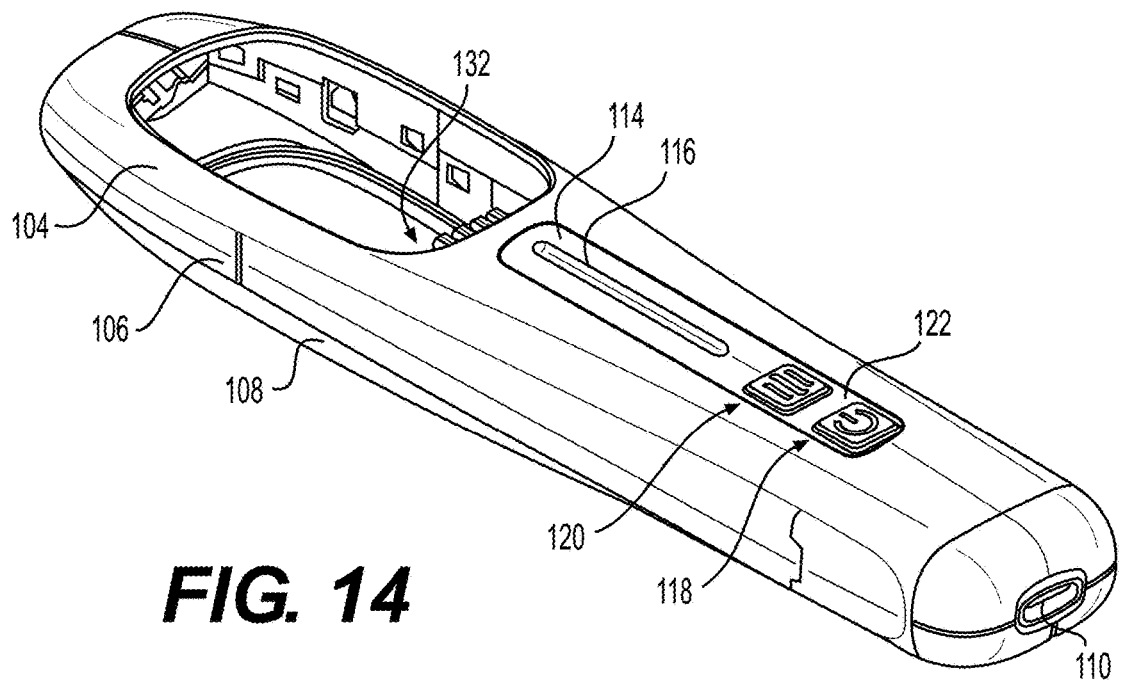
Figure 15:
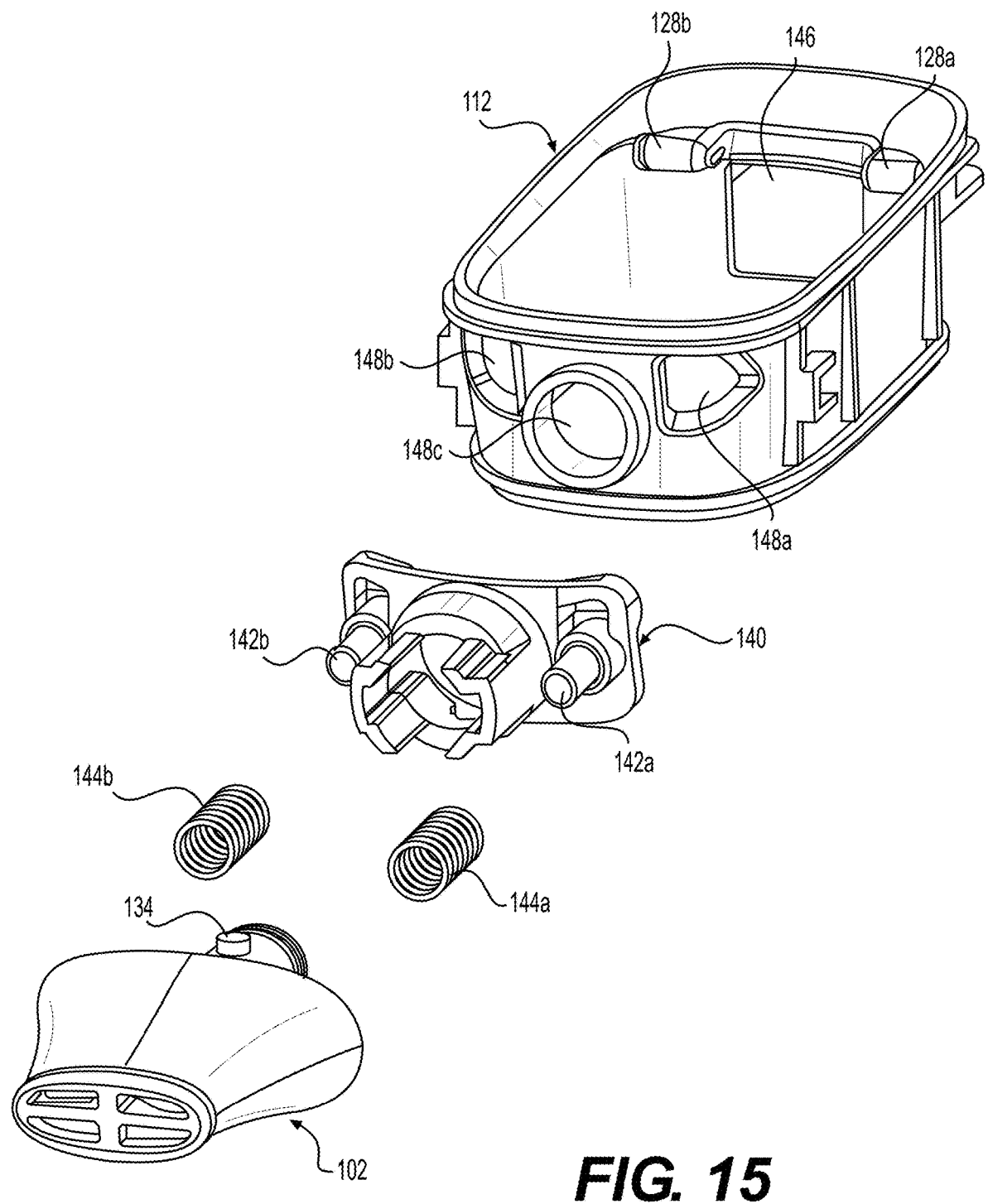
FIG. 15 is an enlarged perspective view of the mouthpiece, springs, retention structure, and bezel structure in FIG. 14.

FIG. 14 is a partially exploded view involving the bezel structure in FIG. 9. FIG. 15 is an enlarged perspective view of the mouthpiece, springs, retention structure, and bezel structure in FIG. 14. Referring to FIGS. 14-15, the bezel structure 112 includes an upstream sidewall and a downstream sidewall. The upstream sidewall of the bezel structure 112 defines a connector opening 146. The connector opening 146 is configured to expose or receive the device electrical connector 132 of the device body 100. The downstream sidewall of the bezel structure 112 defines a first downstream opening 148a, a second downstream opening 148b, and a third downstream opening 148c. The first downstream opening 148a and the second downstream opening 148b of the bezel structure 112 are configured to receive the first downstream protrusion 130a and the second downstream protrusion 130b, respectively, of the retention structure 140. The third downstream opening 148c of the bezel structure 112 is configured to receive the distal end of the mouthpiece 102.

As shown in FIG. 14, the first downstream protrusion 130a and the second downstream protrusion 130b are on the concave side of the retention structure 140. As shown in FIG. 15, a first post 142a and a second post 142b are on the opposing convex side of the retention structure 140. A first spring 144a and a second spring 144b are disposed on the first post 142a and the second post 142b, respectively. The first spring 144a and the second spring 144b are configured to bias the retention structure 140 against the bezel structure 112.

When assembled, the bezel structure 112 may be secured to the frame 106 via a pair of tabs adjacent to the connector opening 146. In addition, the retention structure 140 will abut the bezel structure 112 such that the first downstream protrusion 130a and the second downstream protrusion 130b extend through the first downstream opening 148a and the second downstream opening 148b, respectively. The mouthpiece 102 will be coupled to the retention structure 140 such that the distal end of the mouthpiece 102 extends through the retention structure 140 as well as the third downstream opening 148c of the bezel structure 112. The first spring 144a and the second spring 144b will be between the frame 106 and the retention structure 140.

When a non-nicotine pod assembly 300 is being inserted into the through hole 150 of the device body 100, the downstream end of the non-nicotine pod assembly 300 will push against the first downstream protrusion 130a and the second downstream protrusion 130b of the retention structure 140. As a result, the first downstream protrusion 130a and the second downstream protrusion 130b of the retention structure 140 will resiliently yield and retract from the through hole 150 of the device body 100 (by virtue of compression of the first spring 144a and the second spring 144b), thereby allowing the insertion of the non-nicotine pod assembly 300 to proceed. In an example embodiment, when the first downstream protrusion 130a and the second downstream protrusion 130b are fully retracted from the through hole 150 of the device body 100, the displacement of the retention structure 140 may cause the ends of the first post 142a and the second post 142b to contact the inner end surface of the frame 106. Furthermore, because the mouthpiece 102 is coupled to the retention structure 140, the distal end of the mouthpiece 102 will retract from the through hole 150, thus causing the proximal end of the mouthpiece 102 (e.g., visible portion including the end cover 138) to also shift by a corresponding distance away from the device housing.

Once the non-nicotine pod assembly 300 is adequately inserted such that the first downstream recess and the second downstream recess of the non-nicotine pod assembly 300 reach a position that allows an engagement with the first downstream protrusion 130a and the second downstream protrusion 130b, respectively, the stored energy from the compression of the first spring 144a and the second spring 144b will cause the first downstream protrusion 130a and the second downstream protrusion 130b to resiliently protract and engage with the first downstream recess and the second downstream recess, respectively, of the non-nicotine pod assembly 300. Furthermore, the engagement may produce a haptic and/or auditory feedback (e.g., audible click) to notify an adult vaper that the non-nicotine pod assembly 300 is properly seated within the through hole 150 of the device body 100.

Figure 16:
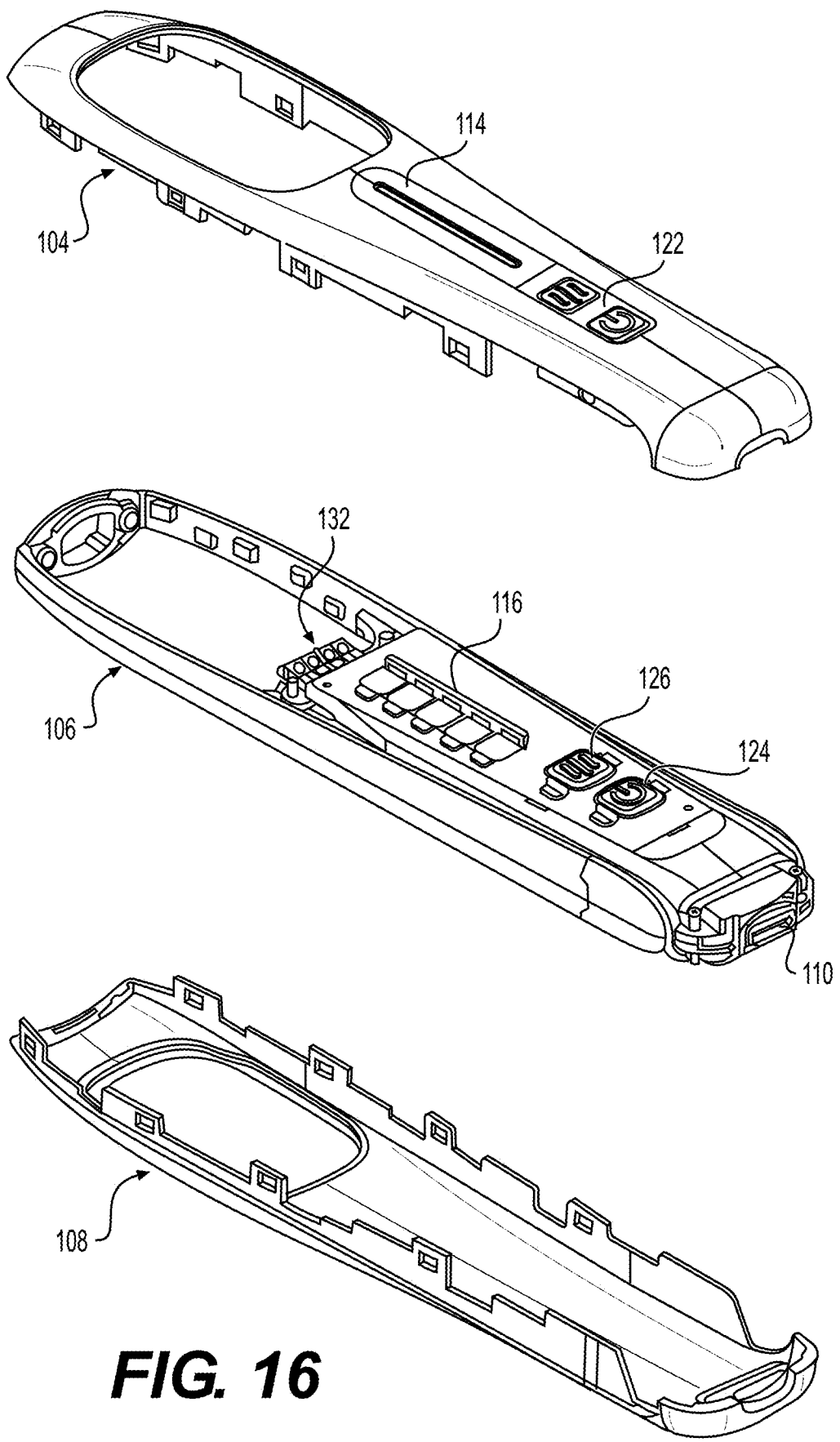
FIG. 16 is a partially exploded view involving the front cover, the frame, and the rear cover in FIG. 14.

FIG. 16 is a partially exploded view involving the front cover, the frame, and the rear cover in FIG. 14. Referring to FIG. 16, various mechanical components, electronic components, and/or circuitry associated with the operation of the non-nicotine e-vaping device 500 may be secured to the frame 106. The front cover 104 and the rear cover 108 may be configured to engage with the frame 106 via a snap-fit arrangement. In an example embodiment, the front cover 104 and the rear cover 108 include clips configured to interlock with corresponding mating members of the frame 106. The clips may be in a form of tabs with orifices configured to receive the corresponding mating members (e.g., protrusions with beveled edges) of the frame 106. In FIG. 16, the front cover 104 has two rows with four clips each (for a total of eight clips for the front cover 104). Similarly, the rear cover 108 has two rows with four clips each (for a total of eight clips for the rear cover 108). The corresponding mating members of the frame 106 may be on the inner sidewalls of the frame 106. As a result, the engaged clips and mating members may be hidden from view when the front cover 104 and the rear cover 108 are snapped together. Alternatively, the front cover 104 and/or the rear cover 108 may be configured to engage with the frame 106 via an interference fit. However, it should be understood that the front cover 104, the frame 106, and the rear cover 108 may be coupled via other suitable arrangements and techniques.

Figure 17:
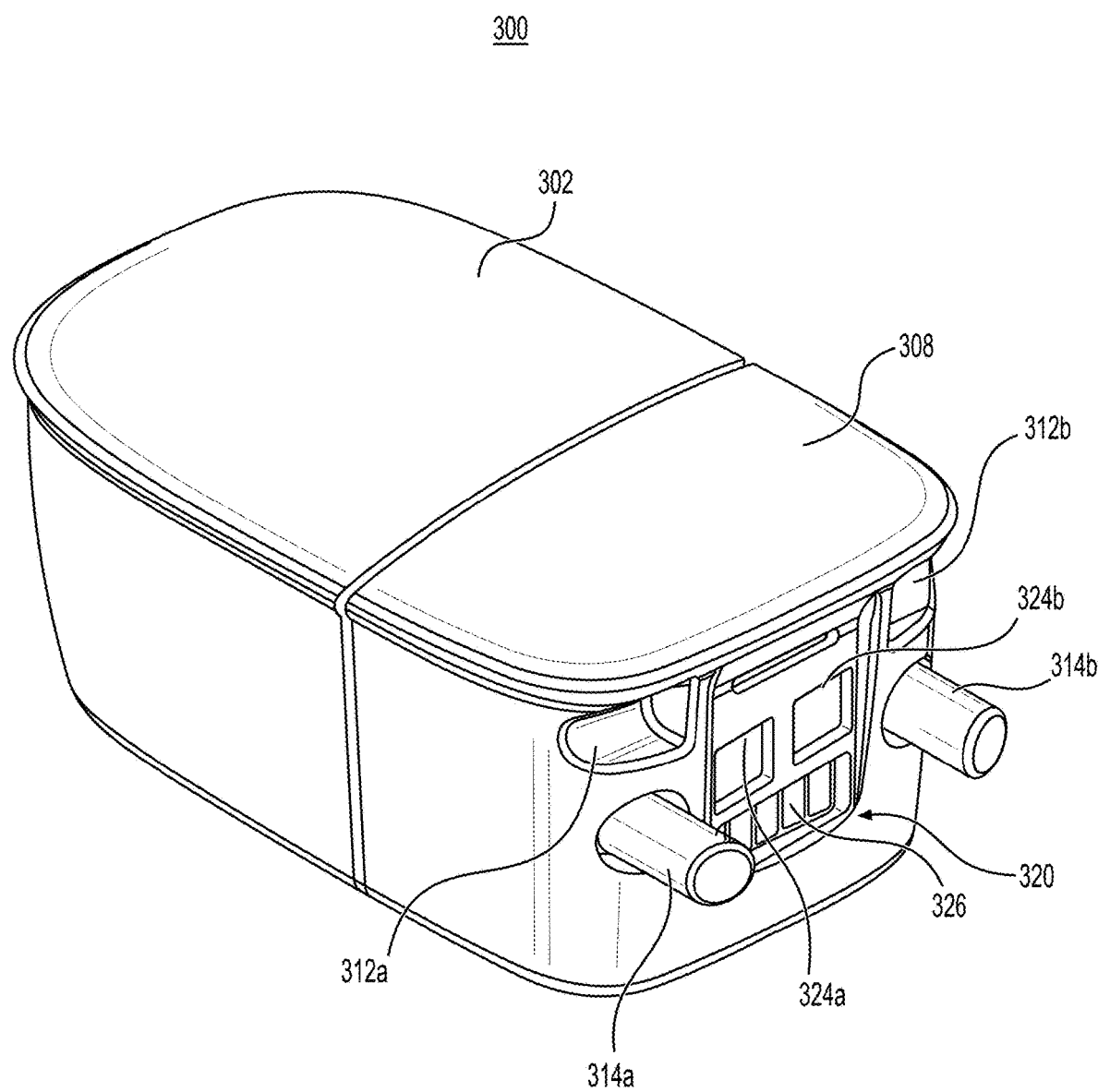
FIG. 17 is a perspective view of the non-nicotine pod assembly of the non-nicotine e-vaping device in FIG. 6.
Figure 18:
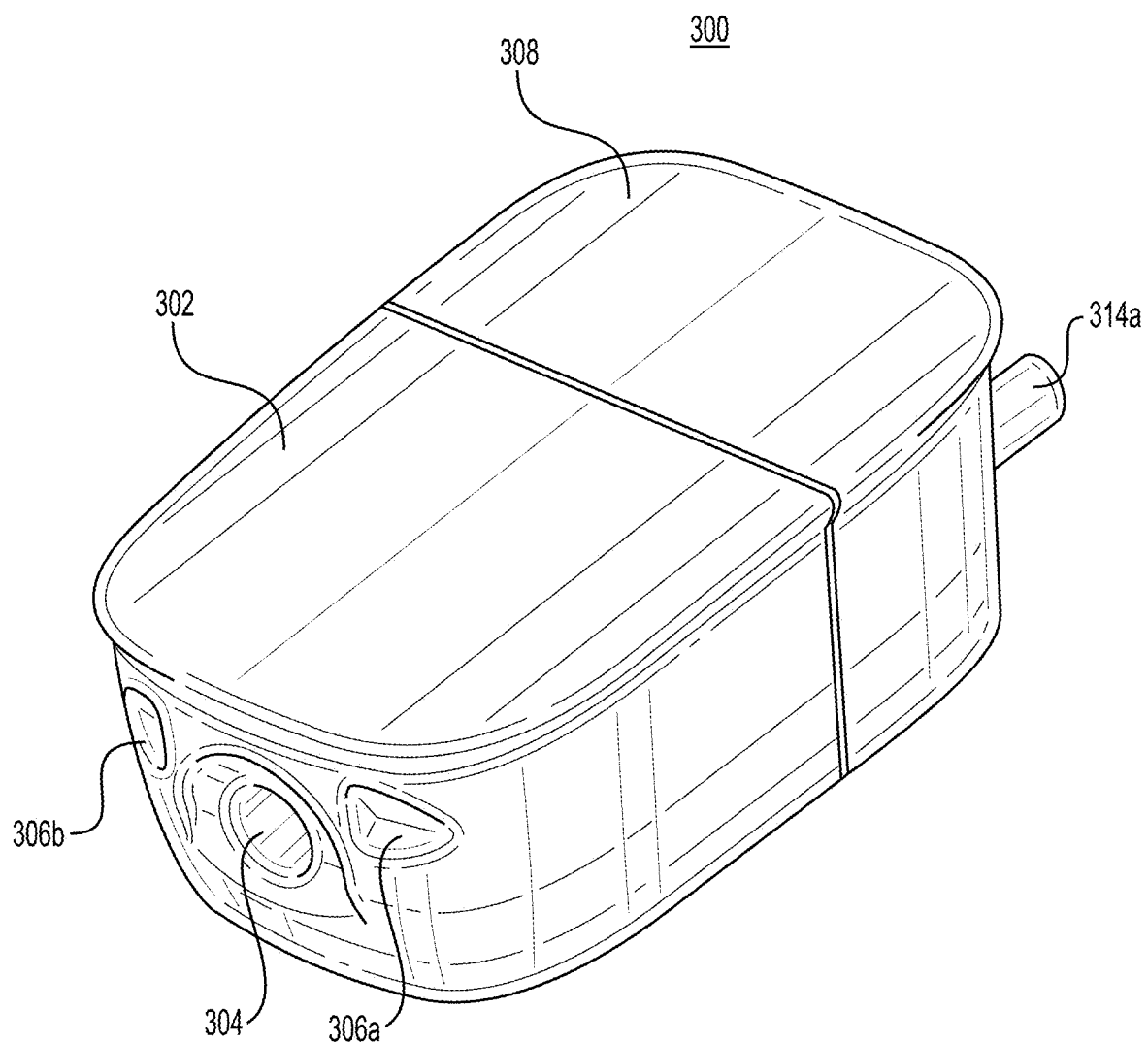
FIG. 18 is another perspective view of the non-nicotine pod assembly of FIG. 17.
Figure 19:
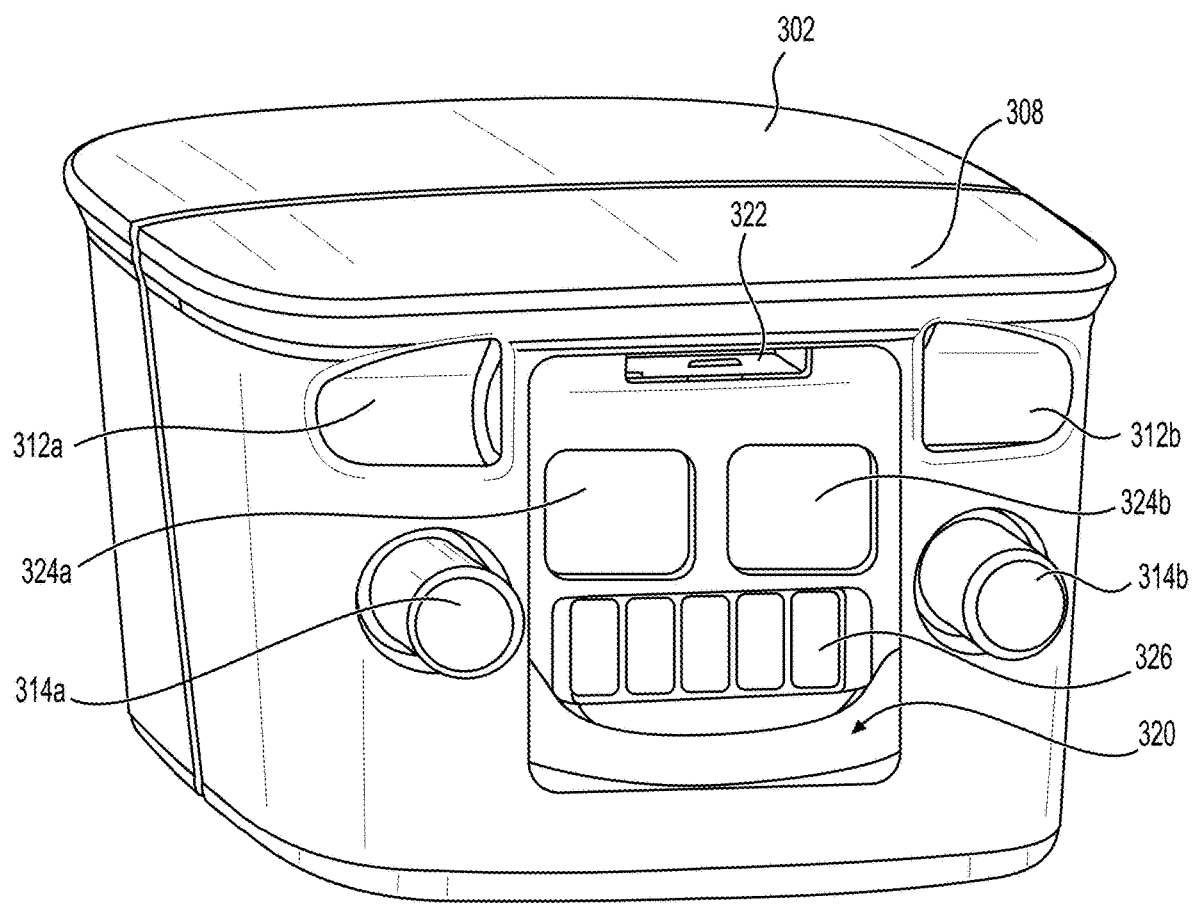
FIG. 19 is another perspective view of the non-nicotine pod assembly of FIG. 18.
Figure 20:
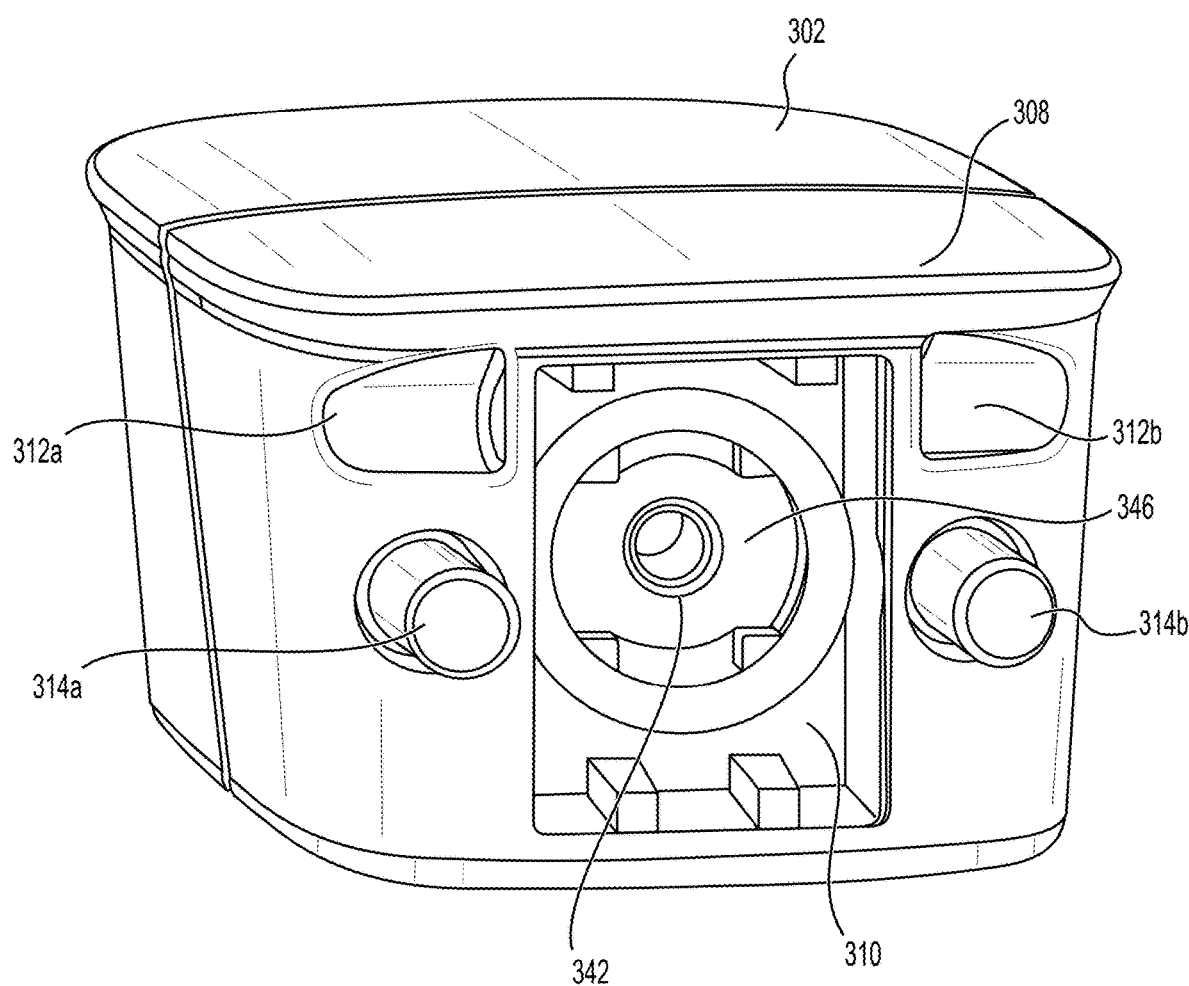
FIG. 20 is a perspective view of the non-nicotine pod assembly of FIG. 19 without the connector module.

FIG. 17 is a perspective view of the non-nicotine pod assembly of the non-nicotine e-vaping device in FIG. 6. FIG. 18 is another perspective view of the non-nicotine pod assembly of FIG. 17. FIG. 19 is another perspective view of the non-nicotine pod assembly of FIG. 18. Referring to FIGS. 17-19, the non-nicotine pod assembly 300 for the non-nicotine e-vaping device 500 includes a pod body configured to hold a non-nicotine pre-vapor formulation. The pod body has an upstream end and a downstream end. The upstream end of the pod body defines a cavity 310 (FIG. 20). The downstream end of the pod body defines a pod outlet 304 that is in fluidic communication with the cavity 310 at the upstream end. A connector module 320 is configured to be seated within the cavity 310 of the pod body. The connector module 320 includes an external face and a side face. The external face of the connector module 320 forms an exterior of the pod body.

The external face of the connector module 320 defines a pod inlet 322. The pod inlet 322 (through which air enters during vaping) is in fluidic communication with the pod outlet 304 (through which a non-nicotine vapor exits during vaping). The pod inlet 322 is shown in FIG. 19 as being in a form of a slot. However, it should be understood that example embodiments are not limited thereto and that other forms are possible. When the connector module 320 is seated within the cavity 310 of the pod body, the external face of the connector module 320 remains visible, while the side face of the connector module 320 becomes mostly obscured so as to be only partially viewable through the pod inlet 322 based on a given angle.

The external face of the connector module 320 includes at least one electrical contact. The at least one electrical contact may include a plurality of power contacts. For instance, the plurality of power contacts may include a first power contact 324a and a second power contact 324b. The first power contact 324a of the non-nicotine pod assembly 300 is configured to electrically connect with the first pair of power contacts (e.g., the pair adjacent to the first upstream protrusion 128a in FIG. 12) of the device electrical connector 132 of the device body 100. Similarly, the second power contact 324b of the non-nicotine pod assembly 300 is configured to electrically connect with the second pair of power contacts (e.g., the pair adjacent to the second upstream protrusion 128b in FIG. 12) of the device electrical connector 132 of the device body 100. In addition, the at least one electrical contact of the non-nicotine pod assembly 300 includes a plurality of data contacts 326. The plurality of data contacts 326 of the non-nicotine pod assembly 300 are configured to electrically connect with the data contacts of the device electrical connector 132 (e.g., row of five projections in FIG. 12). While two power contacts and five data contacts are shown in connection with the non-nicotine pod assembly 300, it should be understood that other variations are possible depending on the design of the device body 100.

In an example embodiment, the non-nicotine pod assembly 300 includes a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The external face of the connector module 320 may be regarded as being part of the upstream end face of the non-nicotine pod assembly 300. The front face of the non-nicotine pod assembly 300 may be wider and longer than the rear face. In such an instance, the first side face and the second side face may be angled inwards towards each other. The upstream end face and the downstream end face may also be angled inwards towards each other. Because of the angled faces, the insertion of the non-nicotine pod assembly 300 will be unidirectional (e.g., from the front side (side associated with the front cover 104) of the device body 100). As a result, the possibility that the non-nicotine pod assembly 300 will be improperly inserted into the device body 100 can be reduced or prevented.

As illustrated, the pod body of the non-nicotine pod assembly 300 includes a first housing section 302 and a second housing section 308. The first housing section 302 has a downstream end defining the pod outlet 304. The rim of the pod outlet 304 may optionally be a sunken or indented region. In such an instance, this region may resemble a cove, wherein the side of the rim adjacent to the rear face of the non-nicotine pod assembly 300 may be open, while the side of the rim adjacent to the front face may be surrounded by a raised portion of the downstream end of the first housing section 302. The raised portion may function as a stopper for the distal end of the mouthpiece 102. As a result, this configuration for the pod outlet 304 may facilitate the receiving and aligning of the distal end of the mouthpiece 102 (e.g., FIG. 11) via the open side of the rim and its subsequent seating against the raised portion of the downstream end of the first housing section 302. In a non-limiting embodiment, the distal end of the mouthpiece 102 may also include (or be formed of) a resilient material to help create a seal around the pod outlet 304 when the non-nicotine pod assembly 300 is properly inserted within the through hole 150 of the device body 100.

The downstream end of the first housing section 302 additionally defines at least one downstream recess. In an example embodiment, the at least one downstream recess is in a form of a first downstream recess 306a and a second downstream recess 306b. The pod outlet 304 may be between the first downstream recess 306a and the second downstream recess 306b. The first downstream recess 306a and the second downstream recess 306b are configured to engage with the first downstream protrusion 130a and the second downstream protrusion 130b, respectively, of the device body 100. As shown in FIG. 11, the first downstream protrusion 130a and the second downstream protrusion 130b of the device body 100 may be disposed on adjacent corners of the downstream sidewall of the through hole 150. The first downstream recess 306a and the second downstream recess 306b may each be in a form of a V-shaped notch. In such an instance, each of the first downstream protrusion 130a and the second downstream protrusion 130b of the device body 100 may be in a form of a wedge-shaped structure configured to engage with a corresponding V-shaped notch of the first downstream recess 306a and the second downstream recess 306b. The first downstream recess 306a may abut the corner of the downstream end face and the first side face, while the second downstream recess 306b may abut the corner of the downstream end face and the second side face. As a result, the edges of the first downstream recess 306a and the second downstream recess 306b adjacent to the first side face and the second side face, respectively, may be open. In such an instance, as shown in FIG. 18, each of the first downstream recess 306a and the second downstream recess 306b may be a 3-sided recess.

Figure 21:
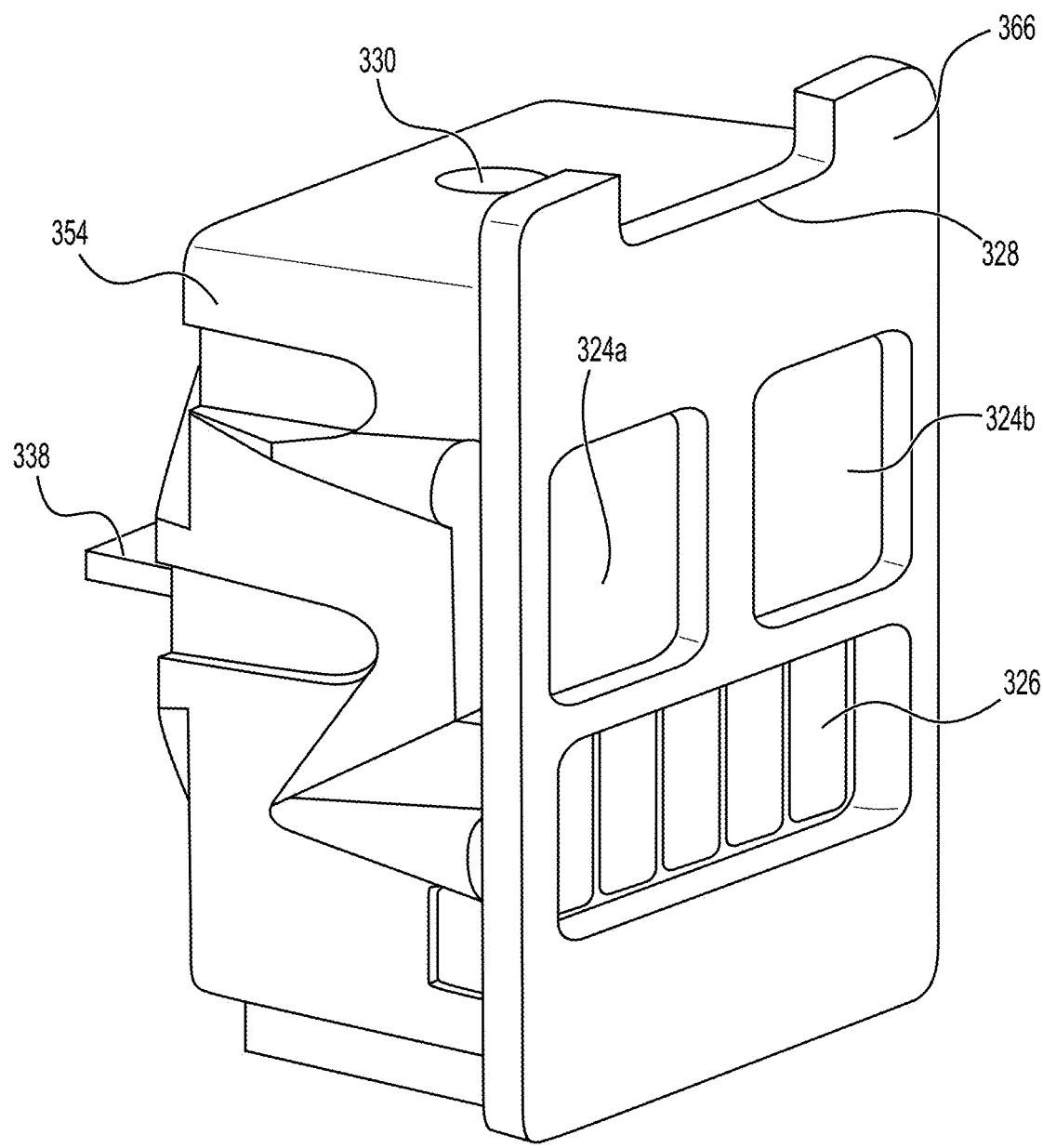
FIG. 21 is a perspective view of the connector module in FIG. 19.

The second housing section 308 has an upstream end defining the cavity 310 (FIG. 20). The cavity 310 is configured to receive the connector module 320 (FIG. 21). In addition, the upstream end of the second housing section 308 defines at least one upstream recess. In an example embodiment, the at least one upstream recess is in a form of a first upstream recess 312a and a second upstream recess 312b. The pod inlet 322 may be between the first upstream recess 312a and the second upstream recess 312b. The first upstream recess 312a and the second upstream recess 312b are configured to engage with the first upstream protrusion 128a and the second upstream protrusion 128b, respectively, of the device body 100. As shown in FIG. 12, the first upstream protrusion 128a and the second upstream protrusion 128b of the device body 100 may be disposed on adjacent corners of the upstream sidewall of the through hole 150. A depth of each of the first upstream recess 312a and the second upstream recess 312b may be greater than a depth of each of the first downstream recess 306a and the second downstream recess 306b. A terminus of each of the first upstream recess 312a and the second upstream recess 312b may also be more rounded than a terminus of each of the first downstream recess 306a and the second downstream recess 306b. For instance, the first upstream recess 312a and the second upstream recess 312b may each be in a form of a U-shaped indentation. In such an instance, each of the first upstream protrusion 128a and the second upstream protrusion 128b of the device body 100 may be in a form of a rounded knob configured to engage with a corresponding U-shaped indentation of the first upstream recess 312a and the second upstream recess 312b. The first upstream recess 312a may abut the corner of the upstream end face and the first side face, while the second upstream recess 312b may abut the corner of the upstream end face and the second side face. As a result, the edges of the first upstream recess 312a and the second upstream recess 312b adjacent to the first side face and the second side face, respectively, may be open.

The first housing section 302 may define a reservoir within configured to hold the non-nicotine pre-vapor formulation. The reservoir may be configured to hermetically seal the non-nicotine pre-vapor formulation until an activation of the non-nicotine pod assembly 300 to release the non-nicotine pre-vapor formulation from the reservoir. As a result of the hermetic seal, the non-nicotine pre-vapor formulation may be isolated from the environment as well as the internal elements of the non-nicotine pod assembly 300 that may potentially react with the non-nicotine pre-vapor formulation, thereby reducing or preventing the possibility of adverse effects to the shelf-life and/or sensorial characteristics (e.g., flavor) of the non-nicotine pre-vapor formulation. The second housing section 308 may contain structures configured to activate the non-nicotine pod assembly 300 and to receive and heat the non-nicotine pre-vapor formulation released from the reservoir after the activation.

The non-nicotine pod assembly 300 may be activated manually by an adult vaper prior to the insertion of the non-nicotine pod assembly 300 into the device body 100. Alternatively, the non-nicotine pod assembly 300 may be activated as part of the insertion of the non-nicotine pod assembly 300 into the device body 100. In an example embodiment, the second housing section 308 of the pod body includes a perforator configured to release the non-nicotine pre-vapor formulation from the reservoir during the activation of the non-nicotine pod assembly 300. The perforator may be in a form of a first activation pin 314a and a second activation pin 314b, which will be discussed in more detail herein.

To activate the non-nicotine pod assembly 300 manually, an adult vaper may press the first activation pin 314a and the second activation pin 314b inward (e.g., simultaneously or sequentially) prior to inserting the non-nicotine pod assembly 300 into the through hole 150 of the device body 100. For instance, the first activation pin 314a and the second activation pin 314b may be manually pressed until the ends thereof are substantially even with the upstream end face of the non-nicotine pod assembly 300. In an example embodiment, the inward movement of the first activation pin 314a and the second activation pin 314b causes a seal of the reservoir to be punctured or otherwise compromised so as to release the non-nicotine pre-vapor formulation therefrom.

Alternatively, to activate the non-nicotine pod assembly 300 as part of the insertion of the non-nicotine pod assembly 300 into the device body 100, the non-nicotine pod assembly 300 is initially positioned such that the first upstream recess 312a and the second upstream recess 312b are engaged with the first upstream protrusion 128a and the second upstream protrusion 128b, respectively (e.g., upstream engagement). Because each of the first upstream protrusion 128a and the second upstream protrusion 128b of the device body 100 may be in a form of a rounded knob configured to engage with a corresponding U-shaped indentation of the first upstream recess 312a and the second upstream recess 312b, the non-nicotine pod assembly 300 may be subsequently pivoted with relative ease about the first upstream protrusion 128a and the second upstream protrusion 128b and into the through hole 150 of the device body 100.

With regard to the pivoting of the non-nicotine pod assembly 300, the axis of rotation may be regarded as extending through the first upstream protrusion 128a and the second upstream protrusion 128b and oriented orthogonally to a longitudinal axis of the device body 100. During the initial positioning and subsequent pivoting of the non-nicotine pod assembly 300, the first activation pin 314a and the second activation pin 314b will come into contact with the upstream sidewall of the through hole 150 and transition from a protracted state to a retracted state as the first activation pin 314a and the second activation pin 314b are pushed (e.g., simultaneously) into the second housing section 308 as the non-nicotine pod assembly 300 progresses into the through hole 150. When the downstream end of the non-nicotine pod assembly 300 reaches the vicinity of the downstream sidewall of the through hole 150 and comes into contact with the first downstream protrusion 130a and the second downstream protrusion 130b, the first downstream protrusion 130a and the second downstream protrusion 130b will retract and then resiliently protract (e.g., spring back) when the positioning of the non-nicotine pod assembly 300 allows the first downstream protrusion 130a and the second downstream protrusion 130b of the device body 100 to engage with the first downstream recess 306a and the second downstream recess 306b, respectively, of the non-nicotine pod assembly 300 (e.g., downstream engagement).

As noted supra, according to an example embodiment, the mouthpiece 102 is secured to the retention structure 140 (of which the first downstream protrusion 130a and the second downstream protrusion 130b are a part). In such an instance, the retraction of the first downstream protrusion 130a and the second downstream protrusion 130b from the through hole 150 will cause a simultaneous shift of the mouthpiece 102 by a corresponding distance in the same direction (e.g., downstream direction). Conversely, the mouthpiece 102 will spring back simultaneously with the first downstream protrusion 130a and the second downstream protrusion 130b when the non-nicotine pod assembly 300 has been sufficiently inserted to facilitate downstream engagement. In addition to the resilient engagement by the first downstream protrusion 130a and the second downstream protrusion 130b, the distal end of the mouthpiece 102 is configured to also be biased against the non-nicotine pod assembly 300 (and aligned with the pod outlet 304 so as to form a relatively vapor-tight seal) when the non-nicotine pod assembly 300 is properly seated within the through hole 150 of the device body 100.

Furthermore, the downstream engagement may produce an audible click and/or a haptic feedback to indicate that the non-nicotine pod assembly 300 is properly seated within the through hole 150 of the device body 100. When properly seated, the non-nicotine pod assembly 300 will be connected to the device body 100 mechanically, electrically, and fluidically. Although the non-limiting embodiments herein describe the upstream engagement of the non-nicotine pod assembly 300 as occurring before the downstream engagement, it should be understood that the pertinent mating, activation, and/or electrical arrangements may be reversed such that the downstream engagement occurs before the upstream engagement. The engagement of the non-nicotine pod assembly 300 with the device body 100 as well as other aspects of the non-nicotine e-vaping device 500 may also be as described in U.S. application Ser. No. 16/695,563, titled "Non-nicotine Pod Assemblies And Non-nicotine E-vaping Devices", filed Nov. 26, 2019, the entire contents of which is incorporated herein by reference.

FIG. 20 is a perspective view of the non-nicotine pod assembly of FIG. 19 without the connector module. Referring to FIG. 20, the upstream end of the second housing section 308 defines a cavity 310. As noted supra, the cavity 310 is configured to receive the connector module 320 (e.g., via interference fit). In an example embodiment, the cavity 310 is situated between the first upstream recess 312a and the second upstream recess 312b and also situated between the first activation pin 314a and the second activation pin 314b. In the absence of the connector module 320, an insert 342 (FIG. 24) and an absorbent material 346 (FIG. 25) are visible through a recessed opening in the cavity 310. The insert 342 is configured to retain the absorbent material 346. The absorbent material 346 is configured to absorb and hold a quantity of the non-nicotine pre-vapor formulation released from the reservoir when the non-nicotine pod assembly 300 is activated. The insert 342 and the absorbent material 346 will be discussed in more detail herein.

Figure 22:
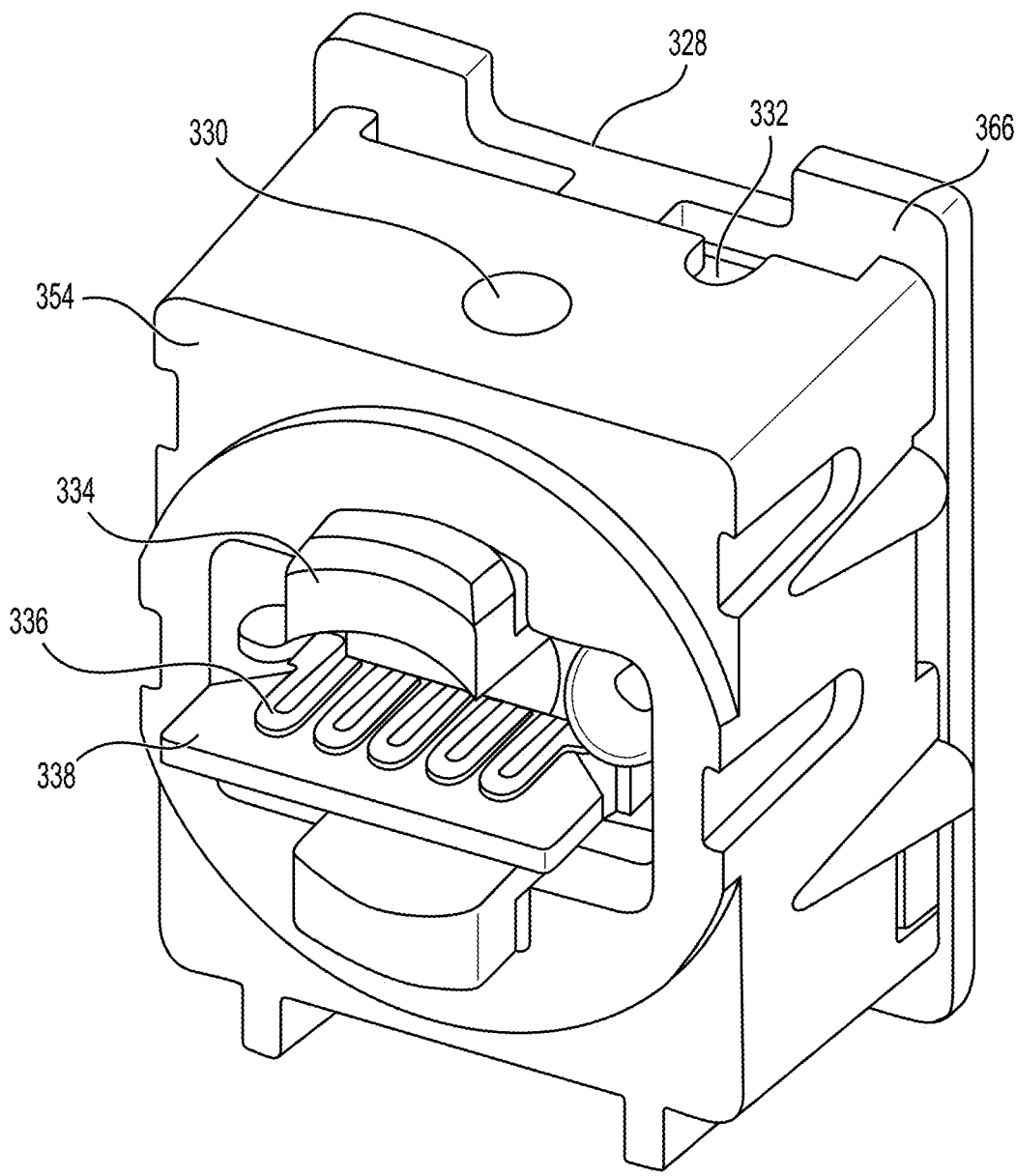
FIG. 22 is another perspective view of the connector module of FIG. 21.

FIG. 21 is a perspective view of the connector module in FIG. 19. FIG. 22 is another perspective view of the connector module of FIG. 21. Referring to FIGS. 21-22, the general framework of the connector module 320 includes a module housing 354 and a face plate 366. In addition, the connector module 320 has a plurality of faces, including an external face and a side face, wherein the external face is adjacent to the side face. In an example embodiment, the external face of the connector module 320 is composed of upstream surfaces of the face plate 366, the first power contact 324a, the second power contact 324b, and the data contacts 326. The side face of the connector module 320 is part of the module housing 354. The side face of the connector module 320 defines a first module inlet 330 and a second module inlet 332. Furthermore, the two lateral faces adjacent to the side face (which are also part of the module housing 354) may include rib structures (e.g., crush ribs) configured to facilitate an interference fit when the connector module 320 is seated within the cavity 310 of the pod body. For instance, each of the two lateral faces may include a pair of rib structures that taper away from the face plate 366. As a result, the module housing 354 will encounter increasing resistance via the friction of the rib structures against the lateral walls of the cavity 310 as the connector module 320 is pressed into the cavity 310 of the pod body. When the connector module 320 is seated within the cavity 310, the face plate 366 may be substantially flush with the upstream end of the second housing section 308. Also, the side face (which defines the first module inlet 330 and the second module inlet 332) of the connector module 320 will be facing a sidewall of the cavity 310.

The face plate 366 of the connector module 320 may have a grooved edge 328 that, in combination with a corresponding side surface of the cavity 310, defines the pod inlet 322. However, it should be understood that example embodiments are not limited thereto. For instance, the face plate 366 of the connector module 320 may be alternatively configured so as to entirely define the pod inlet 322. The side face (which defines the first module inlet 330 and the second module inlet 332) of the connector module 320 and the sidewall of the cavity 310 (which faces the side face) define an intermediate space in between. The intermediate space is downstream from the pod inlet 322 and upstream from the first module inlet 330 and the second module inlet 332. Thus, in an example embodiment, the pod inlet 322 is in fluidic communication with both the first module inlet 330 and the second module inlet 332 via the intermediate space. The first module inlet 330 may be larger than the second module inlet 332. In such an instance, when incoming air is received by the pod inlet 322 during vaping, the first module inlet 330 may receive a primary flow (e.g., larger flow) of the incoming air, while the second module inlet 332 may receive a secondary flow (e.g., smaller flow) of the incoming air.

As shown in FIG. 22, the connector module 320 includes a wick 338 that is configured to transfer a non-nicotine pre-vapor formulation to a heater 336. The heater 336 is configured to heat the non-nicotine pre-vapor formulation during vaping to generate a non-nicotine vapor. The heater 336 may be mounted in the connector module 320 via a contact core 334. The heater 336 is electrically connected to at least one electrical contact of the connector module 320. For instance, one end (e.g., first end) of the heater 336 may be connected to the first power contact 324a, while the other end (e.g., second end) of the heater 336 may be connected to the second power contact 324b. In an example embodiment, the heater 336 includes a folded heating element. In such an instance, the wick 338 may have a planar form configured to be held by the folded heating element. When the connector module 320 is seated within the cavity 310 of the pod body, the wick 338 is configured to be in fluidic communication with the absorbent material 346 such that the non-nicotine pre-vapor formulation that will be in the absorbent material 346 (when the non-nicotine pod assembly 300 is activated) will be transferred to the wick 338 via capillary action.

Figure 23:
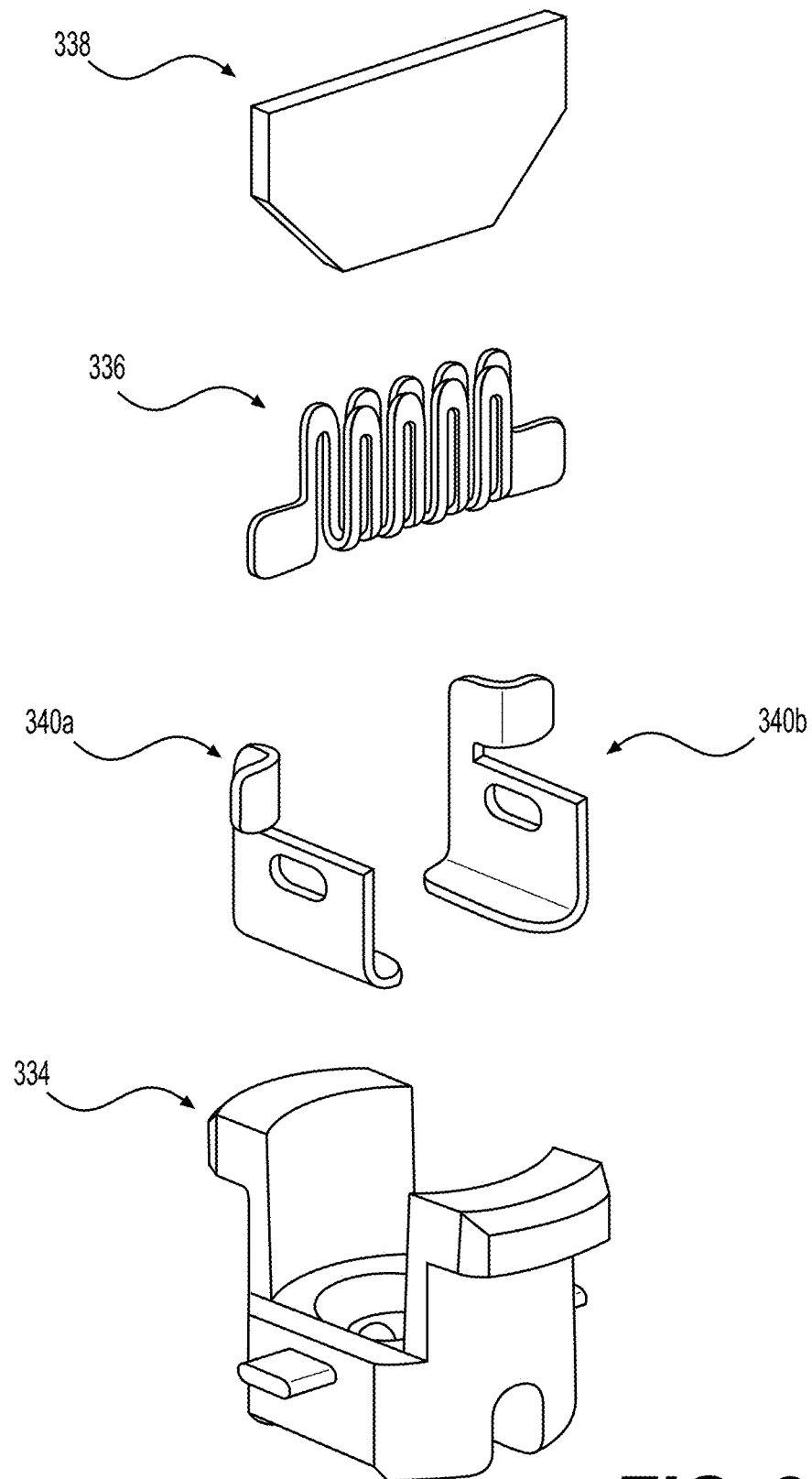
FIG. 23 is an exploded view involving the wick, heater, electrical leads, and contact core in FIG. 22.

FIG. 23 is an exploded view involving the wick, heater, electrical leads, and contact core in FIG. 22. Referring to FIG. 23, the wick 338 may be a fibrous pad or other structure with pores/interstices designed for capillary action. In addition, the wick 338 may have a shape of an irregular hexagon, although example embodiments are not limited thereto. The wick 338 may be fabricated into the hexagonal shape or cut from a larger sheet of material into this shape. Because the lower section of the wick 338 is tapered towards the winding section of the heater 336, the likelihood of the non-nicotine pre-vapor formulation being in a part of the wick 338 that continuously evades vaporization (due to its distance from the heater 336) can be reduced or avoided.

In an example embodiment, the heater 336 is configured to undergo Joule heating (which is also known as ohmic/resistive heating) upon the application of an electric current thereto. Stated in more detail, the heater 336 may be formed of one or more conductors (resistive materials) and configured to produce heat when an electric current passes therethrough. The electric current may be supplied from a power source (e.g., battery) within the device body 100 and conveyed to the heater 336 via the first power contact 324a and the first electrical lead 340a (or via the second power contact 324b and the second electrical lead 340b).

Suitable conductors (resistive materials) for the heater 336 include an iron-based alloy (e.g., stainless steel) and/or a nickel-based alloy (e.g., nichrome). The heater 336 may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain the form of the heater 336 shown in the drawings, the winding pattern may be folded so as to grip the wick 338.

The heater 336 may be secured to the contact core 334 with a first electrical lead 340a and a second electrical lead 340b. The contact core 334 is formed of an insulating material and configured to electrically isolate the first electrical lead 340a from the second electrical lead 340b. In an example embodiment, the first electrical lead 340a and the second electrical lead 340b each define a female aperture that is configured to engage with corresponding male members of the contact core 334. Once engaged, the first end and the second end of the heater 336 may be secured (e.g., welded, soldered, brazed) to the first electrical lead 340a and the second electrical lead 340b, respectively. The contact core 334 may then be seated within a corresponding socket in the module housing 354 (e.g., via interference fit). Upon completion of the assembly of the connector module 320, the first electrical lead 340a will electrically connect a first end of the heater 336 with the first power contact 324a, while the second electrical lead 340b will electrically connect a second end of the heater 336 with the second power contact 324b. The heater and associated structures are discussed in more detail in U.S. application Ser. No. 15/729,909, titled "Folded Heater For Electronic Vaping Device", filed Oct. 11, 2017, the entire contents of which is incorporated herein by reference.

Figure 24:
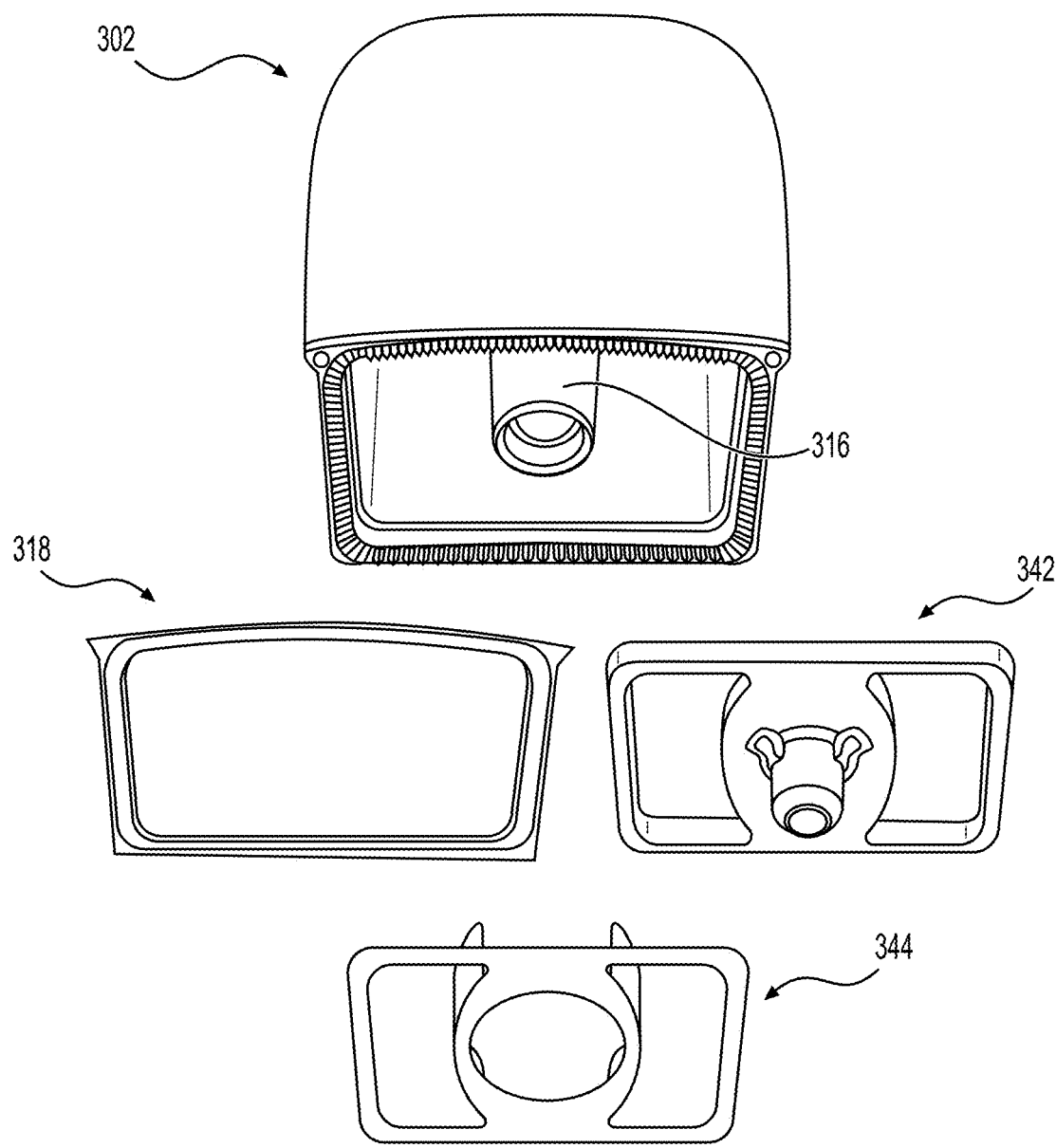
FIG. 24 is an exploded view involving the first housing section of the non-nicotine pod assembly of FIG. 17.

FIG. 24 is an exploded view involving the first housing section of the non-nicotine pod assembly of FIG. 17. Referring to FIG. 24, the first housing section 302 includes a vapor channel 316. The vapor channel 316 is configured to receive a non-nicotine vapor generated by the heater 336 and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. A wrap 318, an insert 342, and a seal 344 are disposed at an upstream end of the first housing section 302 to define the reservoir of the non-nicotine pod assembly 300. For instance, the wrap 318 may be disposed on the rim of the first housing section 302. The insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the reservoir.

In an example embodiment, the insert 342 includes a holder portion that projects from the upstream side (as shown in FIG. 24) and a connector portion that projects from the downstream side (hidden from view in FIG. 24). The holder portion of the insert 342 is configured to hold the absorbent material 346, while the connector portion of the insert 342 is configured to engage with the vapor channel 316 of the first housing section 302. The connector portion of the insert 342 may be configured to be seated within the vapor channel 316 and, thus, engage the interior of the vapor channel 316. Alternatively, the connector portion of the insert 342 may be configured to receive the vapor channel 316 and, thus, engage with the exterior of the vapor channel 316. The insert 342 also defines reservoir outlets through which the non-nicotine pre-vapor formulation flows when the seal 344 is punctured (as shown in FIG. 24) during the activation of the non-nicotine pod assembly 300. The holder portion and the connector portion of the insert 342 may be between the reservoir outlets (e.g., first and second reservoir outlets), although example embodiments are not limited thereto. Furthermore, the insert 342 defines a vapor conduit extending through the holder portion and the connector portion. As a result, when the insert 342 is seated within the first housing section 302, the vapor conduit of the insert 342 will be aligned with and in fluidic communication with the vapor channel 316 so as to form a continuous path through the reservoir to the pod outlet 304 for the non-nicotine vapor generated by the heater 336 during vaping.

The seal 344 is attached to the upstream side of the insert 342 so as to cover the reservoir outlets in the insert 342. In an example embodiment, the seal 344 defines an opening (e.g., central opening) configured to provide the pertinent clearance to accommodate the holder portion (that projects from the upstream side of the insert 342) when the seal 344 is attached to the insert 342. In FIG. 24, it should be understood that the seal 344 is shown in a punctured state. In particular, when punctured by the first activation pin 314a and the second activation pin 314b of the non-nicotine pod assembly 300, the two punctured sections of the seal 344 will be pushed into the reservoir as flaps (as shown in FIG. 24), thus creating two punctured openings (e.g., one on each side of the central opening) in the seal 344. The size and shape of the punctured openings in the seal 344 may correspond to the size and shape of the reservoir outlets in the insert 342. In contrast, when in an unpunctured state, the seal 344 will have a planar form and only one opening (e.g., central opening). The seal 344 is designed to be strong enough to remain intact during the normal movement and/or handling of the non-nicotine pod assembly 300 so as to avoid being prematurely/inadvertently breached. For instance, the seal 344 may be a coated foil (e.g., aluminum-backed polyethylene terephthalate (PET)).

Figure 25:
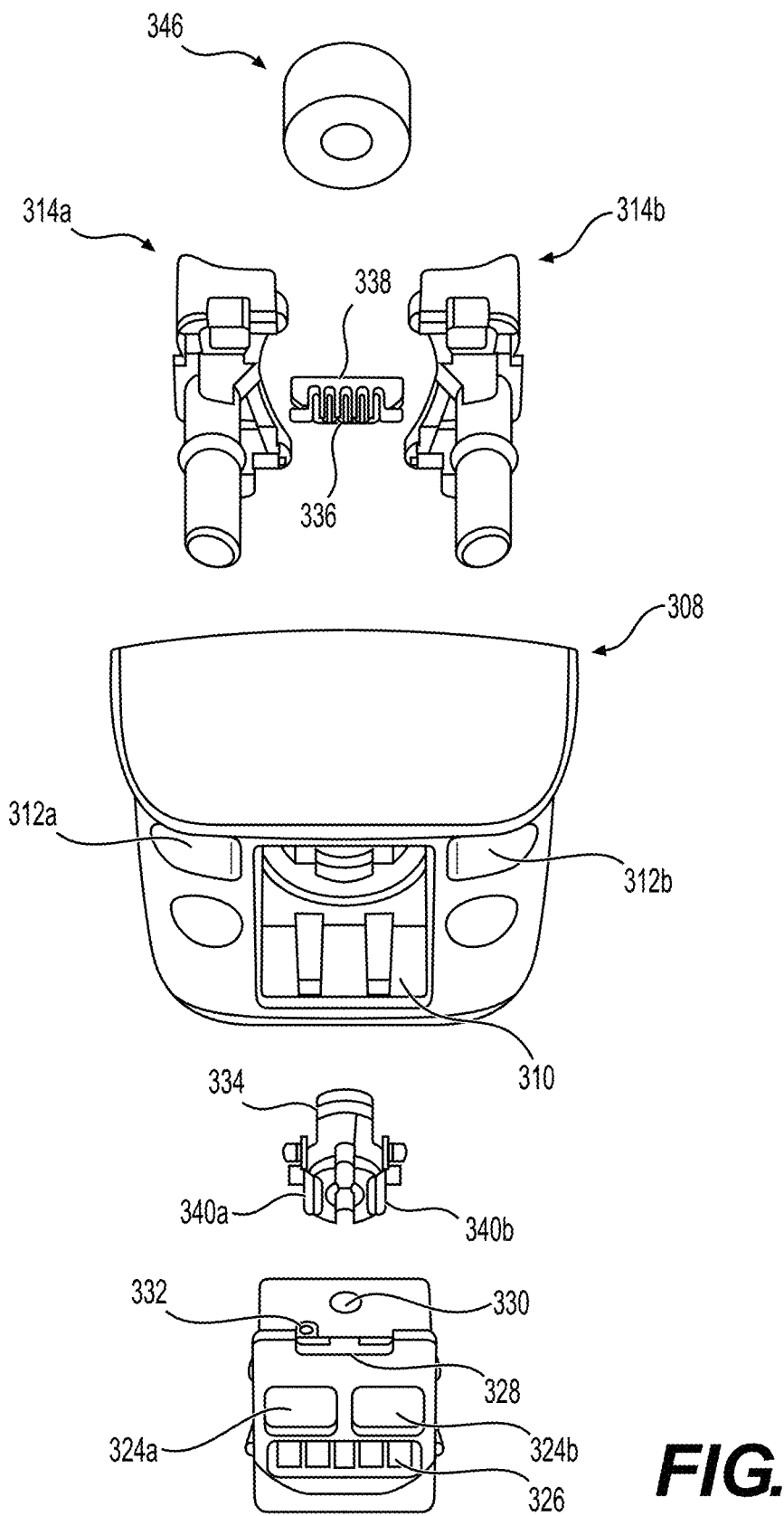
FIG. 25 is a partially exploded view involving the second housing section of the non-nicotine pod assembly of FIG. 17.

FIG. 25 is a partially exploded view involving the second housing section of the non-nicotine pod assembly of FIG. 17. Referring to FIG. 25, the second housing section 308 is structured to contain various components configured to release, receive, and heat the non-nicotine pre-vapor formulation. For instance, the first activation pin 314a and the second activation pin 314b are configured to puncture the reservoir in the first housing section 302 to release the non-nicotine pre-vapor formulation. Each of the first activation pin 314a and the second activation pin 314b has a distal end that extends through corresponding openings in the second housing section 308. In an example embodiment, the distal ends of the first activation pin 314a and the second activation pin 314b are visible after assembly (e.g., FIG. 17), while the remainder of the first activation pin 314a and the second activation pin 314b are hidden from view within the non-nicotine pod assembly 300. In addition, each of the first activation pin 314a and the second activation pin 314b has a proximal end that is positioned so as to be adjacent to and upstream from the seal 344 prior to activation of the non-nicotine pod assembly 300. When the first activation pin 314a and the second activation pin 314b are pushed into the second housing section 308 to activate the non-nicotine pod assembly 300, the proximal end of each of the first activation pin 314a and the second activation pin 314b will advance through the insert 342 and, as a result, puncture the seal 344, which will release the non-nicotine pre-vapor formulation from the reservoir. The movement of the first activation pin 314a may be independent of the movement of the second activation pin 314b (and vice versa). The first activation pin 314a and the second activation pin 314b will be discussed in more detail herein.

The absorbent material 346 is configured to engage with the holder portion of the insert 342 (which, as shown in FIG. 24, projects from the upstream side of the insert 342). The absorbent material 346 may have an annular form, although example embodiments are not limited thereto. As depicted in FIG. 25, the absorbent material 346 may resemble a hollow cylinder. In such an instance, the outer diameter of the absorbent material 346 may be substantially equal to (or slightly larger than) the length of the wick 338. The inner diameter of the absorbent material 346 may be smaller than the average outer diameter of the holder portion of the insert 342 so as to result in an interference fit. To facilitate the engagement with the absorbent material 346, the tip of the holder portion of the insert 342 may be tapered. In addition, although hidden from view in FIG. 25, the downstream side of the second housing section 308 may define a concavity configured receive and support the absorbent material 346. An example of such a concavity may be a circular chamber that is in fluidic communication with and downstream from the cavity 310. The absorbent material 346 is configured to receive and hold a quantity of the non-nicotine pre-vapor formulation released from the reservoir when the non-nicotine pod assembly 300 is activated.

The wick 338 is positioned within the non-nicotine pod assembly 300 so as to be in fluidic communication with the absorbent material 346 such that the non-nicotine pre-vapor formulation can be drawn from the absorbent material 346 to the heater 336 via capillary action. The wick 338 may physically contact an upstream side of the absorbent material 346 (e.g., bottom of the absorbent material 346 based on the view shown in FIG. 25). In addition, the wick 338 may be aligned with a diameter of the absorbent material 346, although example embodiments are not limited thereto.

As illustrated in FIG. 25 (as well as previous FIG. 23), the heater 336 may have a folded configuration so as to grip and establish thermal contact with the opposing surfaces of the wick 338. The heater 336 is configured to heat the wick 338 during vaping to generate a non-nicotine vapor. To facilitate such heating, the first end of the heater 336 may be electrically connected to the first power contact 324a via the first electrical lead 340a, while the second end of the heater 336 may be electrically connected to the second power contact 324b via the second electrical lead 340b. As a result, an electric current may be supplied from a power source (e.g., battery) within the device body 100 and conveyed to the heater 336 via the first power contact 324a and the first electrical lead 340a (or via the second power contact 324b and the second electrical lead 340b). The first electrical lead 340a and the second electrical lead 340b (which are shown separately in FIG. 23) may be engaged with the contact core 334 (as shown in FIG. 25). The relevant details of other aspects of the connector module 320, which is configured to be seated within the cavity 310 of the second housing section 308, that have been discussed supra (e.g., in connection with FIGS. 21-22) and will not be repeated in this section in the interest of brevity. During vaping, the non-nicotine vapor generated by the heater 336 is drawn through the vapor conduit of the insert 342, through the vapor channel 316 of the first housing section 302, out the pod outlet 304 of the non-nicotine pod assembly 300, and through the vapor passage 136 of the mouthpiece 102 to the vapor outlet(s).

Figure 26:
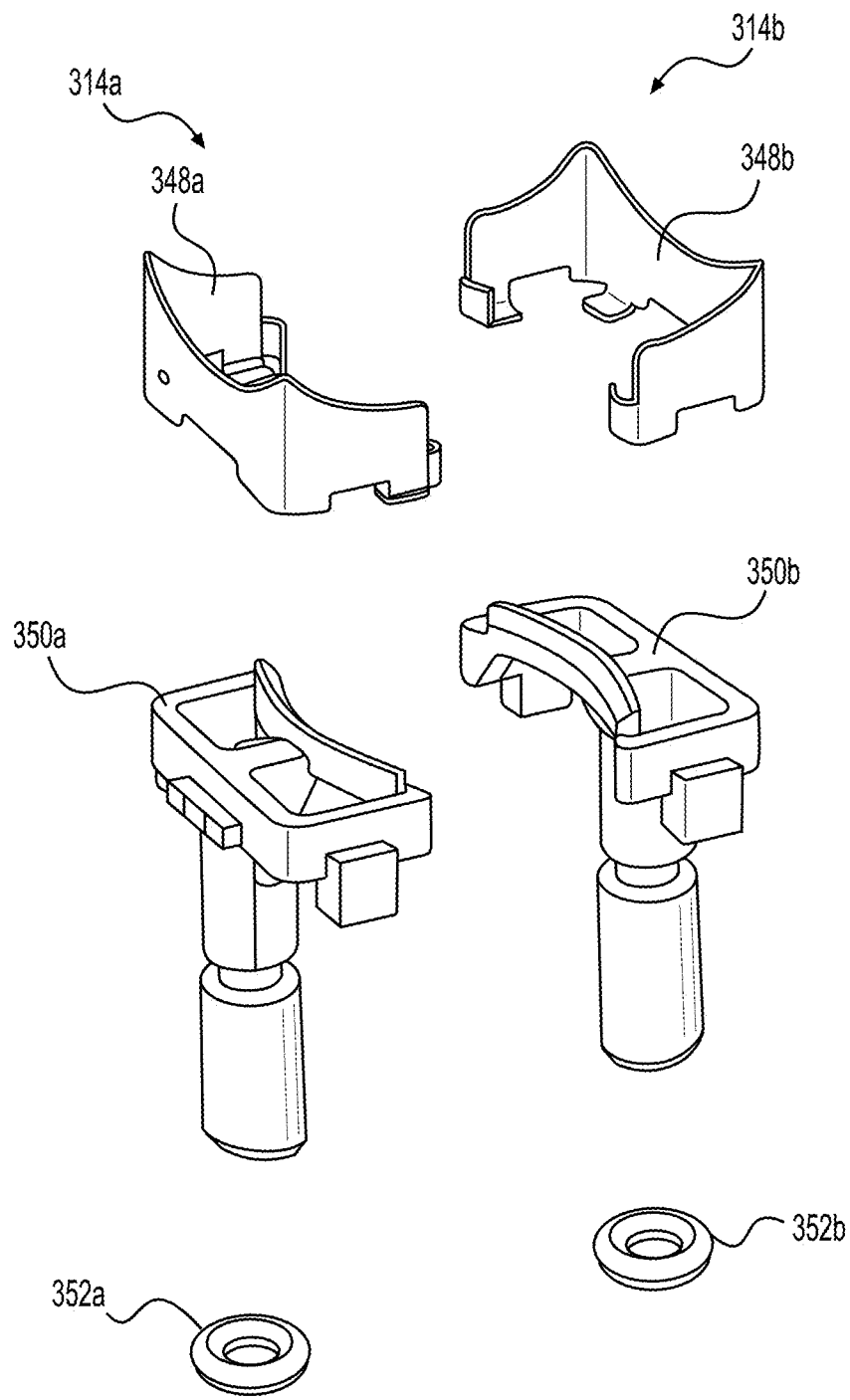
FIG. 26 is an exploded view of the activation pin in FIG. 25.

FIG. 26 is an exploded view of the activation pin in FIG. 25. Referring to FIG. 26, the activation pin may be in the form of a first activation pin 314a and a second activation pin 314b. While two activation pins are shown and discussed in connection with the non-limiting embodiments herein, it should be understood that, alternatively, the non-nicotine pod assembly 300 may include only one activation pin. In FIG. 26, the first activation pin 314a may include a first blade 348a, a first actuator 350a, and a first O-ring 352a. Similarly, the second activation pin 314b may include a second blade 348b, a second actuator 350b, and a second O-ring 352b.

In an example embodiment, the first blade 348a and the second blade 348b are configured to be mounted or attached to upper portions (e.g., proximal portions) of the first actuator 350a and the second actuator 350b, respectively. The mounting or attachment may be achieved via a snap-fit connection, an interference fit (e.g., friction fit) connection, an adhesive, or other suitable coupling technique. The top of each of the first blade 348a and the second blade 348b may have one or more curved or concave edges that taper upward to a pointed tip. For instance, each of the first blade 348a and the second blade 348b may have two pointed tips with a concave edge therebetween and a curved edge adjacent to each pointed tip. The radii of curvature of the concave edge and the curved edges may be the same, while their arc lengths may differ. The first blade 348a and the second blade 348b may be formed of a sheet metal (e.g., stainless steel) that is cut or otherwise shaped to have the desired profile and bent to its final form. In another instance, the first blade 348a and the second blade 348b may be formed of plastic.

Based on a plan view, the size and shape of the first blade 348a, the second blade 348b, and portions of the first actuator 350a and the second actuator 350b on which they are mounted may correspond to the size and shape of the reservoir outlets in the insert 342. Additionally, as shown in FIG. 26, the first actuator 350a and the second actuator 350b may include projecting edges (e.g., curved inner lips which face each other) configured to push the two punctured sections of the seal 344 into the reservoir as the first blade 348a and the second blade 348b advance into the reservoir. In a non-limiting embodiment, when the first activation pin 314a and the second activation pin 314b are fully inserted into the non-nicotine pod assembly 300, the two flaps (from the two punctured sections of the seal 344, as shown in FIG. 24) may be between the curved sidewalls of the reservoir outlets of the insert 342 and the corresponding curvatures of the projecting edges of the first actuator 350a and the second actuator 350b. As a result, the likelihood of the two punctured openings in the seal 344 becoming obstructed (by the two flaps from the two punctured sections) may be reduced or prevented. Furthermore, the first actuator 350a and the second actuator 350b may be configured to guide the non-nicotine pre-vapor formulation from the reservoir toward the absorbent material 346.

The lower portion (e.g., distal portion) of each of the first actuator 350a and the second actuator 350b is configured to extend through a bottom section (e.g., upstream end) of the second housing section 308. This rod-like portion of each of the first actuator 350a and the second actuator 350b may also be referred to as the shaft. The first O-ring 352a and the second O-ring 352b may be seated in annular grooves in the respective shafts of the first actuator 350a and the second actuator 350b. The first O-ring 352a and the second O-ring 352b are configured to engage with the shafts of the first actuator 350a and the second actuator 350b as well as the inner surfaces of the corresponding openings in the second housing section 308 in order to provide a fluid-tight seal. As a result, when the first activation pin 314a and the second activation pin 314b are pushed inward to activate the non-nicotine pod assembly 300, the first O-ring 352a and the second O-ring 352b may move together with the respective shafts of the first actuator 350a and the second actuator 350b within the corresponding openings in the second housing section 308 while maintaining their respective seals, thereby helping to reduce or prevent leakage of the non-nicotine pre-vapor formulation through the openings in the second housing section 308 for the first activation pin 314a and the second activation pin 314b. The first O-ring 352a and the second O-ring 352b may be formed of silicone.

Figure 27:
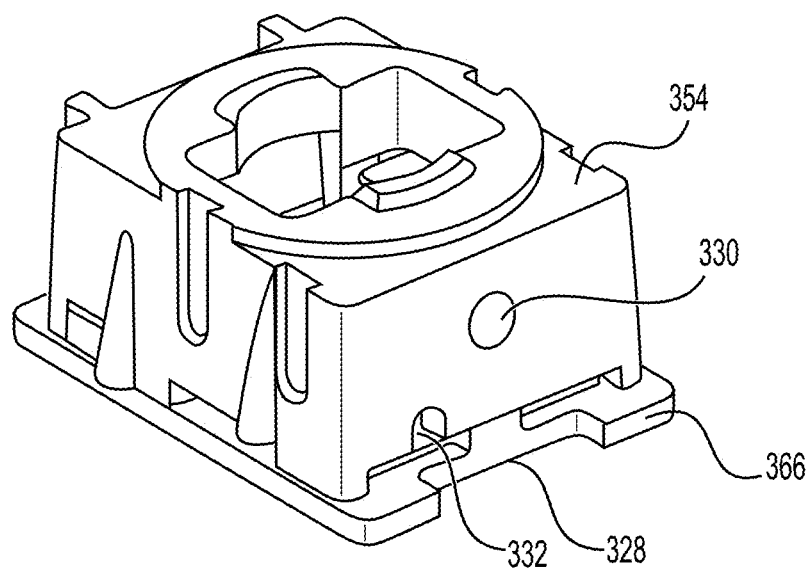
FIG. 27 is a perspective view of the connector module of FIG. 22 without the wick, heater, electrical leads, and contact core.
Figure 28:
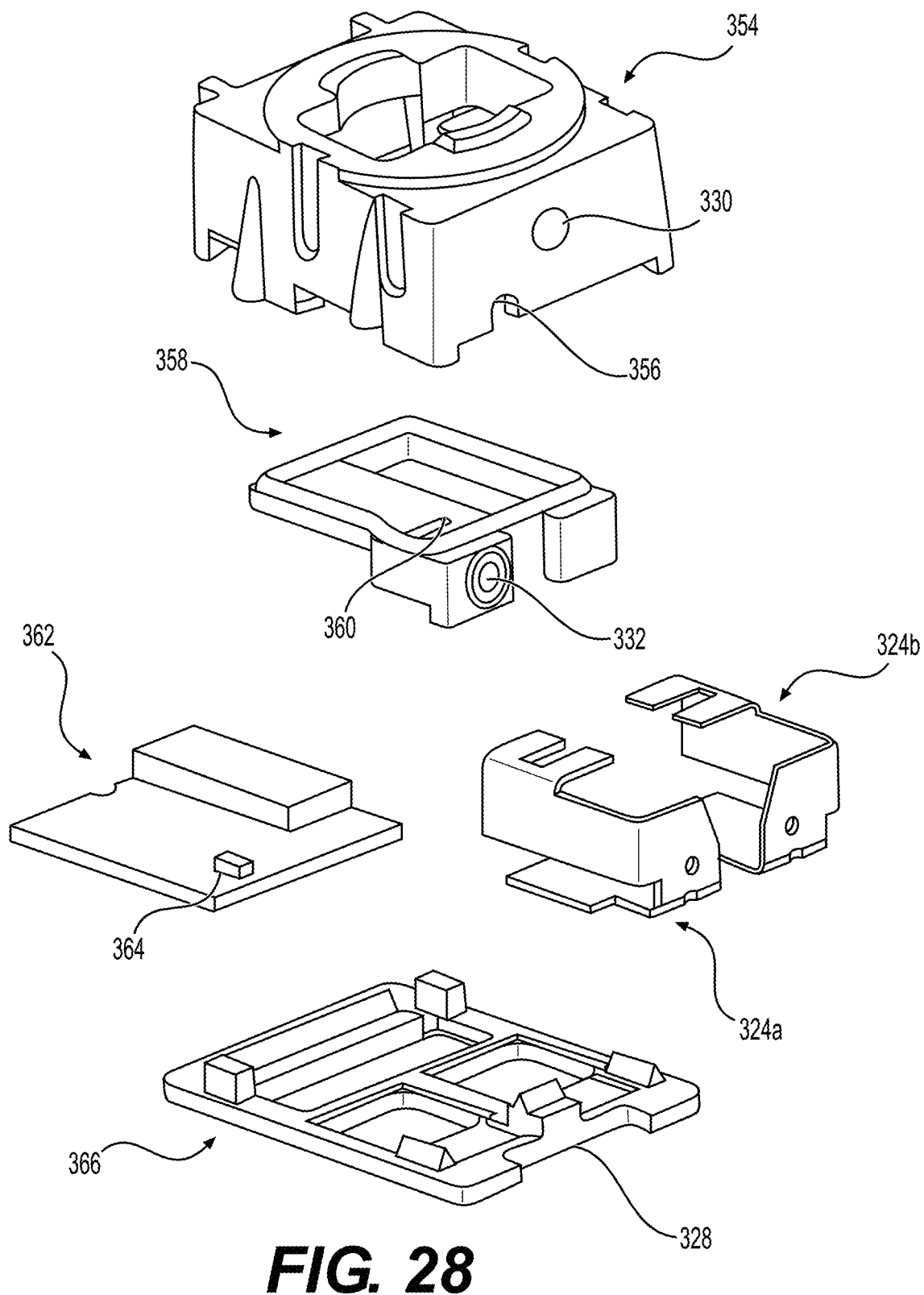
FIG. 28 is an exploded view of the connector module of FIG. 27.

FIG. 27 is a perspective view of the connector module of FIG. 22 without the wick, heater, electrical leads, and contact core. FIG. 28 is an exploded view of the connector module of FIG. 27. Referring to FIGS. 27-28, the module housing 354 and the face plate 366 generally form the exterior framework of the connector module 320. The module housing 354 defines the first module inlet 330 and a grooved edge 356. The grooved edge 356 of the module housing 354 exposes the second module inlet 332 (which is defined by the bypass structure 358). However, it should be understood that the grooved edge 356 may also be regarded as defining a module inlet (e.g., in combination with the face plate 366). The face plate 366 has a grooved edge 328 which, together with the corresponding side surface of the cavity 310 of the second housing section 308, defines the pod inlet 322. In addition, the face plate 366 defines a first contact opening, a second contact opening, and a third contact opening. The first contact opening and the second contact opening may be square-shaped and configured to expose the first power contact 324a and the second power contact 324b, respectively, while the third contact opening may be rectangular-shaped and configured to expose the plurality of data contacts 326, although example embodiments are not limited thereto.

The first power contact 324a, the second power contact 324b, a printed circuit board (PCB) 362, and the bypass structure 358 are disposed within the exterior framework formed by the module housing 354 and the face plate 366. The printed circuit board (PCB) 362 includes the plurality of data contacts 326 on its upstream side (which is hidden from view in FIG. 28) and a sensor 364 on its downstream side. The bypass structure 358 defines the second module inlet 332 and a bypass outlet 360.

During assembly, the first power contact 324a and the second power contact 324b are positioned so as to be visible through the first contact opening and the second contact opening, respectively, of the face plate 366. Additionally, the printed circuit board (PCB) 362 is positioned such that the plurality of data contacts 326 on its upstream side are visible through the third contact opening of the face plate 366. The printed circuit board (PCB) 362 may also overlap the rear surfaces of the first power contact 324a and the second power contact 324b. The bypass structure 358 is positioned on the printed circuit board (PCB) 362 such that the sensor 364 is within an air flow path defined by the second module inlet 332 and the bypass outlet 360. When assembled, the bypass structure 358 and the printed circuit board (PCB) 362 may be regarded as being surrounded on at least four sides by the meandering structures of the first power contact 324a and the second power contact 324b. In an example embodiment, the bifurcated ends of the first power contact 324a and the second power contact 324b are configured to electrically connect to the first electrical lead 340a and the second electrical lead 340b.

When incoming air is received by the pod inlet 322 during vaping, the first module inlet 330 may receive a primary flow (e.g., larger flow) of the incoming air, while the second module inlet 332 may receive a secondary flow (e.g., smaller flow) of the incoming air. The secondary flow of the incoming air may improve the sensitivity of the sensor 364. After exiting the bypass structure 358 through the bypass outlet 360, the secondary flow rejoins with the primary flow to form a combined flow that is drawn into and through the contact core 334 so as to encounter the heater 336 and the wick 338. In a non-limiting embodiment, the primary flow may be 60-95% (e.g., 80-90%) of the incoming air, while the secondary flow may be 5-40% (e.g., 10-20%) of the incoming air. However, it should be understood that other ranges may be utilized, which may be above or below the ranges disclosed above.

The first module inlet 330 may be a resistance-to-draw (RTD) port, while the second module inlet 332 may be a bypass port. In such a configuration, the resistance-to-draw for the non-nicotine e-vaping device 500 may be adjusted by changing the size of the first module inlet 330 (rather than changing the size of the pod inlet 322). In an example embodiment, the size of the first module inlet 330 may be selected such that the resistance-to-draw is between 25-100 mmH$_2$O (e.g., between 30-50 mmH$_2$O). For instance, a diameter of 1.0 mm for the first module inlet 330 may result in a resistance-to-draw of 88.3 mmH$_2$O. In another instance, a diameter of 1.1 mm for the first module inlet 330 may result in a resistance-to-draw of 73.6 mmH$_2$O. In another instance, a diameter of 1.2 mm for the first module inlet 330 may result in a resistance-to-draw of 58.7 mmH$_2$O. In yet another instance, a diameter of 1.3 mm for the first module inlet 330 may result in a resistance-to-draw of about 40-43 mmH$_2$O. Notably, the size of the first module inlet 330, because of its internal arrangement, may be adjusted without affecting the external aesthetics of the non-nicotine pod assembly 300, thereby allowing for a more standardized product design for non-nicotine pod assemblies with various resistance-to-draw (RTD) while also reducing the likelihood of an inadvertent blockage of the incoming air. The non-nicotine pod assembly 300 as well as other aspects of the non-nicotine e-vaping device 500 may also be as described in U.S. application Ser. No. 16/696,189, titled "Non-nicotine Pod Assemblies And Non-nicotine E-vaping Devices", filed Nov. 26, 2019, and in U.S. application Ser. No. 16/696,081, titled "Non-nicotine Pod Assemblies And Non-nicotine E-vaping Devices", filed Nov. 26, 2019, the entire contents of each of which are incorporated herein by reference.

In an example embodiment, the non-nicotine pre-vapor formulation neither includes tobacco nor is derived from tobacco. A non-nicotine compound of the non-nicotine pre-vapor formulation may be part of, or included in a liquid or a partial-liquid that includes an extract, an oil, an alcohol, a tincture, a suspension, a dispersion, a colloid, a general non-neutral (slightly acidic or slightly basic) solution, or combinations thereof. During the preparation of the non-nicotine pre-vapor formulation, the non-nicotine compound may be infused into, comingled, or otherwise combined with the other ingredients of the non-nicotine pre-vapor formulation.

In an example embodiment, the non-nicotine compound undergoes a slow, natural decarboxylation process over an extended duration of time at relatively low temperatures, including at or below room temperature (e.g., 72° F.). In addition, the non-nicotine compound may undergo a significantly elevated decarboxylation process (e.g., 50% decarboxylation or greater) if exposed to elevated temperatures, especially in the range of about 175° F. or greater over a period of time (minutes or hours) at a relatively low pressure such as 1 atmosphere. Higher temperatures of about 240° F. or greater can cause a rapid or instantaneous decarboxylation to occur at a relatively high decarboxylation rate, although further elevated temperatures can cause a degradation of some or all of the chemical properties of the non-nicotine compound(s).

In an example embodiment, the non-nicotine compound may be from a medicinal plant (e.g., a naturally-occurring constituent of a plant that provides a medically-accepted therapeutic effect). The medicinal plant may be a cannabis plant, and the constituent may be at least one cannabis-derived constituent. Cannabinoids (e.g., phytocannabinoids) and terpenes are examples of cannabis-derived constituents. Cannabinoids interact with receptors in the body to produce a wide range of effects. As a result, cannabinoids have been used for a variety of medicinal purposes. Cannabis-derived materials may include the leaf and/or flower material from one or more species of cannabis plants, or extracts from the one or more species of cannabis plants. For instance, the one or more species of cannabis plants may include *Cannabis sativa, Cannabis indica*, and *Cannabis ruderalis*. In some example embodiments, the non-nicotine pre-vapor formulation includes a mixture of cannabis and/or cannabis-derived constituents that are, or are derived from, 60-80% (e.g., 70%) *Cannabis sativa* and 20-40% (e.g., 30%) *Cannabis indica*.

Non-limiting examples of cannabis-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from the heater may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formula the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

In an example embodiment, at least one flavorant is present in an amount ranging from about 0.2% to about 15% by weight (e.g., about 1% to 12%, about 2% to 10%, or about 5% to 8%) based on a total weight of the non-nicotine pre-vapor formulation. The at least one flavorant may be at least one of a natural flavorant, an artificial flavorant, or a combination of a natural flavorant and an artificial flavorant. The at least one flavorant may include volatile cannabis flavor compounds (flavonoids) or other flavor compounds instead of, or in addition to, the cannabis flavor compounds. For instance, the at least one flavorant may include menthol, wintergreen, peppermint, cinnamon, clove, combinations thereof, and/or extracts thereof. In addition, flavorants may be included to provide other herb flavors, fruit flavors, nut flavors, liquor flavors, roasted flavors, minty flavors, savory flavors, combinations thereof, and any other desired flavors.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A non-nicotine pod assembly for a non-nicotine e-vaping device, comprising:
a pod body configured to hold a non-nicotine pre-vapor formulation, the pod body having an upstream end and a downstream end, the upstream end defining a pod inlet and at least one upstream recess and including a perforator configured to release the non-nicotine pre-vapor formulation, the downstream end defining a pod outlet and at least one downstream recess, the perforator having a proximal end and a distal end opposite the proximal end, the proximal end positioned within the pod body and the distal end extending externally from the upstream end of the pod body.

2. The non-nicotine pod assembly of claim 1, wherein the upstream end is an opposing surface of the pod body from the downstream end.

3. The non-nicotine pod assembly of claim 1, wherein a depth of the at least one upstream recess is greater than a depth of the at least one downstream recess.

4. The non-nicotine pod assembly of claim 1, wherein a terminus of the at least one upstream recess is more rounded than a terminus of the at least one downstream recess.

5. The non-nicotine pod assembly of claim 1, wherein the at least one upstream recess includes two upstream recesses.

6. The non-nicotine pod assembly of claim 5, wherein the pod inlet is between the two upstream recesses.

7. The non-nicotine pod assembly of claim 1, wherein the at least one upstream recess is in a form of a U-shaped indentation.

8. The non-nicotine pod assembly of claim 1, wherein the at least one downstream recess includes two downstream recesses.

9. The non-nicotine pod assembly of claim 8, wherein the pod outlet is between the two downstream recesses.

10. The non-nicotine pod assembly of claim 1, wherein the at least one downstream recess is in a form of a V-shaped notch.

11. The non-nicotine pod assembly of claim 1, wherein the perforator includes at least one activation pin.

* * * * *